(12) United States Patent
Har-Noy

(10) Patent No.: US 9,782,463 B2
(45) Date of Patent: *Oct. 10, 2017

(54) METHOD FOR ALLOGENEIC CELL THERAPY

(71) Applicant: Immunovative Thearpies, Ltd., Jerusalem (IL)

(72) Inventor: Michael Har-Noy, Jerusalem (IL)

(73) Assignee: Immunovative Therapies Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/041,642

(22) Filed: Feb. 11, 2016

(65) Prior Publication Data

US 2016/0158328 A1    Jun. 9, 2016

Related U.S. Application Data

(60) Division of application No. 14/173,494, filed on Feb. 5, 2014, now Pat. No. 9,301,977, which is a division of application No. 13/596,142, filed on Aug. 28, 2012, now Pat. No. 8,679,841, which is a division of application No. 12/869,490, filed on Aug. 26, 2010, now Pat. No. 8,273,377, which is a continuation of application No. 12/172,594, filed on Jul. 14, 2008, now Pat. No. 7,943,180, which is a division of application No. 10/838,454, filed on May 4, 2004, now Pat. No. 7,435,592.

(60) Provisional application No. 60/549,032, filed on Mar. 1, 2004, provisional application No. 60/547,966, filed on Feb. 26, 2004, provisional application No. 60/545,450, filed on Feb. 18, 2004, provisional application No. 60/470,171, filed on May 13, 2003.

(51) Int. Cl.
| | |
|---|---|
| *A61K 35/28* | (2015.01) |
| *A61K 35/26* | (2015.01) |
| *A61K 39/00* | (2006.01) |
| *C12N 5/0783* | (2010.01) |
| *A61K 35/17* | (2015.01) |

(52) U.S. Cl.
CPC .......... *A61K 39/0005* (2013.01); *A61K 35/17* (2013.01); *C12N 5/0636* (2013.01); *A61K 2039/5154* (2013.01); *A61K 2039/57* (2013.01); *C12N 2501/51* (2013.01); *C12N 2501/515* (2013.01); *C12N 2531/00* (2013.01); *C12N 2533/40* (2013.01)

(58) Field of Classification Search
None
See application file for complete search history.

(56) References Cited

U.S. PATENT DOCUMENTS

| | | |
|---|---|---|
| 5,806,529 A | 9/1998 | Reisner et al. |
| 6,352,694 B1 | 3/2002 | June et al. |
| 6,534,055 B1 | 3/2003 | June et al. |
| 6,905,680 B2 | 6/2005 | June et al. |
| 6,905,874 B2 | 6/2005 | Berenson et al. |
| 2002/0115214 A1 | 8/2002 | June |
| 2002/0127208 A1 | 9/2002 | Waller et al. |
| 2004/0228848 A1 | 11/2004 | Har-Noy |
| 2006/0115487 A1 | 6/2006 | Har-Noy |
| 2008/0112975 A1 | 5/2008 | Har-Noy |

FOREIGN PATENT DOCUMENTS

| | | |
|---|---|---|
| JP | 2001-523645 A | 11/2001 |
| JP | 2001522806 A | 11/2001 |
| JP | 2002-521042 A | 7/2002 |
| WO | 94/12196 A1 | 6/1994 |
| WO | 97/05239 A1 | 3/1997 |
| WO | 97/46256 A1 | 12/1997 |
| WO | 99/24045 A1 | 5/1999 |
| WO | 01/62895 A2 | 8/2001 |
| WO | 03015705 A2 | 2/2003 |
| WO | 03/024989 A2 | 3/2003 |
| WO | 03/038062 A2 | 5/2003 |
| WO | 03/057171 A2 | 7/2003 |
| WO | 2004/004768 A1 | 1/2004 |

(Continued)

OTHER PUBLICATIONS

Raghupathy, R. et al. (1999). "Maternal Th1- and Th2-Type Reactivity to Placental Antigens in Normal Human Pregnancy and Unexplained Recurrent Spontaneous Abortions." Cellular Immunology, vol. 196, No. 2: pp. 122-130.

(Continued)

*Primary Examiner* — Michail Belyavskyi

(74) *Attorney, Agent, or Firm* — Westman, Champlin & Koehler, P.A.; Z. Peter Sawicki; Visala Goswitz

(57) ABSTRACT

A method of manipulating allogeneic cells for use in allogeneic cell therapy providing a composition of highly activated allogeneic T-cells which are infused into immunocompetent cancer patients to elicit a novel anti-tumor immune mechanism, or "Mirror Effect". In contrast to current allogeneic cell therapy protocols where T-cells in the graft mediate the beneficial graft vs. tumor (GVT) and detrimental graft vs. host (GVH) effects, the allogeneic cells of the present invention stimulate host T-cells to mediate the "mirror" of these effects. The mirror of the GVT effect is the host vs. tumor (HVT) effect. The "mirror" of the GVH effect is the host vs. graft (HVG) effect The anti-tumor HVT effect occurs in conjunction with a non-toxic HVG rejection effect. The highly activated allogeneic cells of the invention can be used to stimulate host immunity in a complete HLA mismatched setting in a patient.

4 Claims, No Drawings

(56) References Cited

FOREIGN PATENT DOCUMENTS

| WO | 2005/001074 A1 | 1/2005 |
|---|---|---|
| WO | 2005/081982 A2 | 9/2005 |

OTHER PUBLICATIONS

Rondon, G., S. Giralt, et al. (1996). "Graft-versus-leukemia effect after allogeneic bone marrow transplantation for chronic lymphocytic leukemia." Bone Marrow Transplant 18(3): 669-72.

Rosenberg, S. A. (2001). "Progress in the development of immunotherapy for the treatment of patients with cancer." Journal of Internal Medicine, vol. 250, No. 6: pp. 462-475.

Roussel, E. et al. (1996). "Predominance of a type 2 intratumoural immune response in fresh tumour-infiltrating lymphocytes from human gliomas." Clinical and Experimental Immunology, vol. 105, No. 2: pp. 344-352.

Rubbi, C.P. et al. (1993). "Evidence of surface antigen detachment during incubation of cells with immunomagnetic beads." Journal of Immunology Methods, vol. 166, No. 2: pp. 233-241.

Santin, A. D. et al. (2000). "Interleukin-10 Increases Th1 Cytokine Production and Cytotoxic Potential in Human Papillomavirus-Specific CD8(+) Cytotoxic T Lymphocytes." Journal of Virology, vol. 74, No. 10: pp. 4729-4737.

Sato, M., S. Goto, et al. (1998). "Impaired production of Th1 cytokines and increased frequency of Th2 subsets in PBMC from advanced cancer patients." Anticancer Res 18(5D): 3951-5.

Saxton, M. L. et al. (1997). "Adoptive Transfer of Anti-CD3-Activated CD4+ T Cells Plus Cyclophosphamide and Liposome-Encapsulated Interleukin-2 Cure Murine MC-38 and 3LL Tumors and Establish Tumor-Specific Immunity." Blood, vol. 89, No. 7: pp. 2529-2536.

Shibuya, T.Y. et al. (2000). "Anti-CD3/Anti-CD28 Bead Stimulation Overcomes CD3 Unresponsiveness in Patients With Head and Neck Squamous Cell Carcinoma." Arch Otolaryngol Head Neck Surg, vol. 126, No. 4: 473-479.

Shinomiya, Y., M. Harada, et al. (1995). "Anti-metastatic activity induced by the in vivo activation of purified protein derivative (PPD)-recognizing Th1 type CD4+ T cells." Immunobiology 193(5): 439-55.

Shurin, M. R., L. Lu, et al. (1999). "Th1/Th2 balance in cancer, transplantation and pregnancy." Springer Semin Immunopathol 21(3): 339-59.

Slavin, S. et al. (2001). "Non-myeloablative allogeneic Stem cell transplantation focusing on immunotherapy of life-threatening malignant and non-malignant diseases." Critical Reviews Oncology Hematology, vol. 39, No. 1-2: pp. 25-29.

Slavin, S. et al. (1995). "Allogeneic cell therapy for relapsed leukemia after bone marrow transplantation with donor peripheral blood lymphocytes." Experimental Hematology, vol. 23, No. 14: pp. 1553-1562.

Slavin, S. et al. (1996). "Allogeneic Cell Therapy With Donor Peripheral Blood Cells and Recombinant Human Interleukin-2 to Treat Leukemia Relapse After Allogeneic Bone Marrow Transplantation." Blood, vol. 87, No. 6: pp. 2195-1204.

Slavin, S. et al. (1996). "Allogeneic Cell Therapy: The Treatment of Choice for All Hematologic Malignancies Relapsing Post BMT." Blood, vol. 87, No. 9: pp. 4011-4013.

Slavin, S. et al. (2001). "Nonmyeloablative stem cell transplantation for the treatment of cancer and life-threatening nonmalignant disorders: past accomplishments and future goals." Cancer Chemother Pharmacol, vol. 48, (Suppl 1): pp. S79-S84.

Slavin, S. et al. (1998). "Immunotherapy in conjunction with autologous and allogeneic blood or marrow transplantation in lymphoma." Annals of Oncology, vol. 9 (Suppl 1): pp. S31-S39.

Smith, D. R., S. L. Kunkel, et al. (1994). "Production of interleukin-10 by human bronchogenic carcinoma." Am J Pathol 145(1): 18-25.

Smyth, M. J. et al. (2002). "New Aspects of Natural-Killer-Cell Surveillance and Therapy of Cancer." Nature Reviews Cancer, vol. 2, No. 11: pp. 850-861.

Sredni, B. et al. (1995). "Bone Marrow-Sparing and Prevention of Alopecia by AS101 in Non-Small-Cell Lung Cancer Patients Treated with Carboplatin and Etoposide." Journal of Clinical Oncology, vol. 13, No. 9: pp. 2342-2353.

Sredni, B. et al. (1996). "Predominance of TH1 Response in Tumor-Bearing Mice and Cancer Patients Treated with AS101." National Journal of Cancer Institute, vol. 88, No. 18: pp. 1276-1284.

Sredni, B., R. H. Xu, et al. (1996). "The protective role of the immunomodulator AS101 against chemotherapy-induced alopecia studies on human and animal models." Int J Cancer 65(1): 97-103.

Stein, G., W. Henn, et al. (1998). "Modulation of the cellular and humoral immune responses of tumor patients by mistletoe therapy." Eur J Med Res 3(4): 194-202.

Stern, B. V. et al. (2002). "Vaccination with Tumor Peptide in CpG Adjuvant Protects Via IFN-Gamma-Dependent CD4 Cell Immunity." The Journal of Immunology, vol. 168, No. 12: pp. 6099-6105.

Tabata, T. et al. (1999). "Th2 Subset Dominance Among Peripheral Blood T Lymphocytes in Patients with Digestive Cancers." American Journal of Surgery, vol. 177, No. 3: pp. 203-208.

Taga, K. et al. (1993). "Human Interleukin-10 Can Directly Inhibit T-Cell Growth." Blood, vol. 81, No. 11: pp. 2964-2971.

Takeuchi, T. et al. (1997). "Th2-like response and antitumor effect of anti-interleukin-4 mAb in mice bearing renal cell carcinoma." Cancer Immunol Immunother, vol. 43, No. 6: pp. 375-381.

Tanaka, K., K. Kemmotsu, et al. (1998). "[Flow cytometric analysis of helper T cell subsets (Th1 and Th2) in healthy adults]." Rinsho Byori 46(12): 1247-51.

Tanaka, J., M. Imamura, et al. (1997). "The important balance between cytokines derived from type 1 and type 2 helper T cells in the control of graft-versus-host disease." Bone Marrow Transplant 19(6): 571-6.

Tatsumi, T. et al. (2002). "Disease-associated bias in T helper type 1 (Th1)/Th2 CD4(+) T cell responses against MAGE-6 in HLA-DRB10401(+) patients with renal cell carcinoma or melanoma." Journal of Experimental Medicine, vol. 196, No. 5: pp. 619-628.

Terao, H., M. Harada, et al. (1994). "Th1 type CD4+ T cells may be a potent effector against poorly immunogenic syngeneic tumors." Biotherapy 8(2): 143-51.

Tessmar, J. et al. (2003). "The use of poly(ethylene glycol)-block-poly(lactic acid) derived copolymers for the rapid creation of biomimetic surfaces." Biomaterials, vol. 24, No. 24: pp. 4475-4486.

Thanhauser, A., A. Bohle, et al. (1995). "The induction of bacillus-Calmette-Guerin-activated killer cells requires the presence of monocytes and T-helper type-1 cells." Cancer Immunol Immunother 40(2): 103-8.

Thomas, A. K. et al. (2002). "A Cell-Based Artificial Antigen-Presenting Cell Coated with Anti-CD3 and CD28 Antibodies Enables Rapid Expansion and Long-Term Growth of CD4 T Lymphocytes." Clinical Immunology, vol. 105, No. 3: pp. 259-272.

Thomas, E., R. Storb, et al. (1975). "Bone-marrow transplantation (first of two parts)." N Engl J Med 292(16): 832-43.

Thomas, E. D., R. Storb, et al. (1975). "Bone-marrow transplantation (second of two parts)." N Engl J Med 292(17): 895-902.

Tilg, H. et al. (1994). "Interleukin-6 (IL-6) as an Anti-inflammatory Cytokine. Induction of Circulating IL-1 Receptor Antagonist and Soluble Tumor Necrosis Factor Receptor p55." Blood, vol. 83, No. 1: pp. 113-118.

To, W. C. et al. (2000). "Therapeutic Efficacy of Th1 and Th2 L-selectin-CD4+ Tumor-Reactive T Cells." Laryngoscope vol. 110, (10 Pt 1): pp. 1648-1654.

Ueno, N. T., G. Rondon, et al. (1998). "Allogeneic peripheral-blood progenitor-cell transplantation for poor-risk patients with metastatic breast cancer." J Clin Oncol 16(3): 986-93.

Van Besien, K., P. Thall, et al. (1997). "Allogeneic transplantation for recurrent or refractory non-Hodgkin's lymphoma with poor prognostic features after conditioning with thiotepa, busulfan, and cyclophosphamide: experience in 44 consecutive patients." Biol Blood Marrow Transplant 3(3): 150-6.

Voutsadakis, I. A. (2003). "NK cells in allogeneic bone marrow transplantation." Cancer Immunol Immunother, vol. 52, No. 9: pp. 525-534.

(56) References Cited

OTHER PUBLICATIONS

Vowels, B. R. et al. (1994). "Th2 Cytokine mRNA Expression in Skin in Cutaneous T-Cell Lymphoma." The Journal of Investigative Dermatology, vol. 103, No. 5: pp. 669-673.
Wang, Q. et al. (1995). "Selective Cytokine Gene Expression in Renal Cell Carcinoma Tumor Cells and Tumor-Infiltrating Lymphocytes." International Journal of Cancer, vol. 61, No. 6: pp. 780-785.
Weber, K., U. Mengs, et al. (1998). "Effects of a standardized mistletoe preparation on metastatic B16 melanoma colonization in murine lungs." Arzneimittelforschung 48(5): 497-502.
Weiden, P. L. et al. (1981). "Antileukemic Effect of Chronic Graft-Versus-Host Disease: Contribution to Improved Survival After Allogeneic Marrow Transplantation." New England Journal of Medicine, vol. 304 No. 25: pp. 1529-1533.
Whitmore, M. et al. (1999). "LPD lipopolyplex initiates a potent cytokine response and inhibits tumor growth." Gene Therapy, vol. 6, No. 11: pp. 1867-1875.
Wong, B. R. et al. (1999). "Trance is a TNF family member that regulates dendritic cell and osteoclast function." Journal of Leukocyte Biology, vol. 65, No. 6: pp. 715-724.
Woo, E. Y. et al. (2001). "Regulatory CD4(+)CD25(+) T Cells in Tumors from Patients with Early-Stage Non-Small Cell Lung Cancer and Late-Stage Ovarian Cancer." Cancer Research, vol. 61, No. 12: pp. 4766-4772.
Woo, E. Y. et al. (2002). "Cutting edge: Regulatory T Cells from Lung Cancer Patients Directly Inhibit Autologous T cell proliferation." J Immunol 168(9): 4272-6.
Yamamura, M. (1992). "Defining protective responses to pathogens: cytokine profiles in leprosy lesions." Science 255 (5040): 12.
Anderson, P. et al. (1988). "Crosslinking CD3 with CD2 Using Sepharose-Immobilized Antibodies Enhances T Lymphocyte Proliferation." Cellular Immunology, vol. 115, No. 2: pp. 246-256.
Antin, J. H. et al. (1992). "Cytokine Dysregulation and Acute Graft-Versus-Host Disease." Blood, vol. 80, No. 12: pp. 2964-2968.
Asselin-Paturel et al. (1998). "Quantitative Analysis of Th1, Th2 and TGF-β1 Cytokine Expression in Tumor, TIL and PBL of Non-Small Cell Lung Cancer Patients." Int. J. Cancer, vol. 77, No. 1: pp. 7-12.
Bachmann, M. F. et al. (1997). "Distinct Roles for LFA-1 and CD28 During Activation of Naive T Cells: Adhesion Versus Costimulation." Immunity, vol. 7, No. 4: pp. 549-557.
Banu, N. et al. (1999). "TGF-β1 down-regulates induced expression of both class II MHC and B7-1 on primary murine renal tubular epithelial cells." Kidney International, vol. 56, No. 3: pp. 985-994.
Baroja, M.L. et al. (1989). "The Anti-T Cell Monoclonal Antibody 9.3 (Anti-CD28) Provides a Helper Signal and Bypasses the Need for Accessory Cells in T Cell Activation with Immobilized Anti-CD3 and Mitogens." Cellular Immunology, vol. 120, No. 1: pp. 205-217.
Baxevanis, C. N. et al. (2000). "Compromised anti-tumor responses in tumor necrosis factor-α knockout mice." Eur. J. Immunol., vol. 30, No. 7: pp. 1957-1966.
Belardelli, F. et al. (2002). "Cytokines as a link between innate and adaptive antitumor immunity." Trends in Immunology, vol. 23 No. 4: pp. 201-208.
Blazar, B. R. et al. (1997). "Recent advances in graft-versus-host disease (GVHD) prevention." Immunological Reviews, vol. 157: pp. 79-109.
Blazar, B. R. et al. (1998). "Rapamycin Inhibits the Generation of Graft-Versus-Host Disease- and Graft-Versus-Leukemia-Causing T Cells by Interfering with the Production of Th1 or Th1 Cytotoxic Cytokines." Journal of Immunology, vol. 160, No. 11: pp. 5355-5365.
Carayol, G. et al. (1997). "Quantitative Analysis of T Helper 1, T Helper 2, and Inflammatory Cytokine Expression in Patients After Allogeneic Bone Narrow Transplantation: Relationship with the Occurrence of Acute Graft-Versus-Host Disease." Transplantation, vol. 63, No. 9: pp. 1307-1313.
Carpentier, A. F., G. Auf, et al. (2003). "CpG-oligonucleotides for cancer immunotherapy : review of the literature and potential applications in malignant glioma." Front Biosci 8: E115-27.
Chambers, C. A. et al. (1999). "Costimulatory regulation of T cell function." Current Opinion in Cell Biology, vol. 11, No. 2: pp. 203-210.
Champlin, R., I. Khouri, et al. (1999). "Allogeneic hematopoietic transplantation as adoptive immunotherapy. Induction of graft-versus-malignancy as primary therapy." Hematol Oncol Clin North Am 13(5): 1041-57, vii-viii.
Champlin, R., K. van Besien, et al. (2000). "Allogeneic hematopoietic transplantation for chronic lymphocytic leukemia and lymphoma: potential for nonablative preparative regimens." Curr Oncol Rep 2(2): 182-91.
Chang, J. W., M. Peng, et al. (2000). "Induction of Th1 response by dendritic cells pulsed with autologous melanoma apoptotic bodies." Anticancer Res 20(3A): 1329-36.
Chen, Q. et al. (1994). "Production of IL-10 by Melanoma Cells: Examination of its Role in Immunosuppression Mediated by Melanoma." Int. J. Cancer, vol. 56, No. 5: pp. 755-760.
Childs, R. et al. (2002). "Nonmyeloablative Stem Cell Transplantation for Solid Tumors: Expanding the Application of Allogeneic Immunotherapy." Seminars in Hematology, vol. 39, No. 1: pp. 63-71.
Childs, R. et al. (2000). "Regression of metastatic renal-cell carcinoma after nonmyeloablative allogeneic peripheral-blood stem-cell transplantation." The New England Journal of Medicine, vol. 343, No. 11: pp. 750-758.
Childs, R. W. (2000). "Nonmyeloablative allogeneic peripheral blood stem-cell transplantation as immunotherapy for malignant diseases." Cancer J 6(3): 179-87.
Childs, R. W. (2002). "Immunotherapy of solid tumors: nonmyeloablative allogeneic stem cell transplantation." MedGenMed 4(3): 13.
Clerici, M. et al. (1993). "A TH1—>TH2 switch is a critical step in the etiology of HIV infection." Immunology Today, vol. 14, No. 3: pp. 107-111.
Cohen, P. A., L. Peng, et al. (2000). "CD4+ T cells in adoptive immunotherapy and the indirect mechanism of tumor rejection." Crit Rev Immunol 20(1): 17-56.
Damle, N.K. et al. (1989). "Stimulation Via the CD3 and CD28 Molecules Induces Responsiveness to IL-4 in CD4+CD29+CD45R—Memory T Lymphocytes." The Journal of Immunology, vol. 143, No. 6: pp. 1761-1767.
Das, H., S. Imoto, et al. (2001). "Kinetic analysis of cytokine gene expression in patients with GVHD after donor lymphocyte infusion." Bone Marrow Transplant 27(4): 373-80.
Daubener, W. et al. (1995). "Establishment of T-helper type 1- and T-helper type 2-like human Toxoplasma antigen-specific T-cell clones." Immunology, vol. 86, No. 1: pp. 79-84.
Deeths, M. J. et al. (1999). "CD8+ T Cells Become Nonresponsive (Anergic) Following Activation in the Presence of Costimulation." The Journal of Immunology, vol. 163, No. 1: pp. 102-110.
De Vita, F., M. Orditura, et al. (2000). "Serum interleukin-10 is an independent prognostic factor in advanced solid tumors." Oncol Rep 7(2): 357-61.
De Waal Malefyt, R. et al. (1993). "Direct Effects of IL-10 on Subsets of Human CD4+ T Cell Clones and Resting T Cells. Specific Inhibition of IL-2 Production and Proliferation." The Journal of Immunology, vol. 150, No. 11: pp. 4754-4765.
D'Orazio, T. J. et al. (1998). "A Novel Role for TGF-β and IL-10 in the Induction of Immune Privilege." The Journal of Immunology, vol. 160, No. 5: 2089-2098.
Dudley, M. E. et al. (2002). "Cancer Regression and Autoimmunity in Patients After Clonal Repopulation with Antitumor Lymphocytes." Science, vol. 298, No. 5594: pp. 850-854.
Egeter, O. et al. (2000). "Eradication of Disseminated Lymphomas with CpG-DNA Activated T Helper Type 1 Cells from Nontransgenic Mice." Cancer Research, vol. 60, No. 6: 1515-1520.
Eibl, B. et al. (1996). "Evidence for a Graft-Versus-Tumor Effect in a Patient Treated With Marrow Ablative Chemotherapy and Allogeneic Bone Marrow Transplantation for Breast Cancer." Blood, vol. 88, No. 4: pp. 1501-1508.

(56) References Cited

OTHER PUBLICATIONS

Elsasser-Beile, U. et al. (1999). "Semiquantitative analysis of Th1 and Th2 cytokine expression in CD3+, CD4+, and CD8+ renal-cell-carcinoma-infiltrating lymphocytes." Cancer Immunol Immunother, vol. 48, No. 4: pp. 204-208.

Emori, Y., H. Sasaki, et al. (1996). "Effect of Z-100, an immunomodulator extracted from human type tubercle bacilli, on the pulmonary metastases of Lewis lung carcinoma in attempt to regulate suppressor T cells and suppressor factor, IL-4." Biotherapy 9(4): 249-56.

Ertl, B., F. Heigl, et al. (2000). "Lectin-mediated bioadhesion: preparation, stability and caco-2 binding of wheat germ agglutinin-functionalized Poly(D,L-lactic-co-glycolic acid)-microspheres." J Drug Targt 8(3): 173-84.

Fan, X. G., W. E. Liu, et al. (1998). "Circulating Th1 and Th2 cytokines in patients with hepatitis C virus infection." Mediators Inflamm 7(4): 295-7.

Finke, J. H., P. Rayman, et al. (1992). "Characterization of a human renal cell carcinoma specific cytotoxic CD8+ T cell line." J Immunother 11(1): 1-11.

Finke, J. H., P. Rayman, et al. (1994). "Characterization of tumor-infiltrating lymphocyte subsets from human renal cell carcinoma: specific reactivity defined by cytotoxicity, interferon-gamma secretion, and proliferation." J Immunother Emphasis Tumor Immunol 15(2): 91-104.

Flanagan, D. L. et al. (1999). "Th1 Cytokines and NK Cells Participate in the Development of Murine Syngeneic Graft-Versus-Host Disease." The Journal of Immunology, vol. 163, No. 3: pp. 1170-1177.

Fowler, D. H., J. Breglio, et al. (1996). "Allospecific CD4+, Th1/Th2 and CD8+, Tc1/Tc2 populations in murine GVL: type I cells generate GVL and type II cells abrogate GVL." Biol Blood Marrow Transplant 2(3): 118-25.

Fowler, D. H. and R. E. Gress (2000). "Th2 and Tc2 cells in the regulation of GVHD, GVL, and graft rejection: considerations for the allogeneic transplantation therapy of leukemia and lymphoma." Leuk Lymphoma 38(3-4): 221-34.

Frassoni, F., M. Labopin, et al. (1996). "Results of allogeneic bone marrow transplantation for acute leukemia have improved in Europe with time—a report of the acute leukemia working party of the European group for blood and marrow transplantation (EBMT)." Bone Marrow Transplant 17(1): 13-8.

Freeman, G. J. et al. (2002). "Protect the killer: CTLs need defenses against the tumor." Nature Medicine, vol. 8, No. 8: pp. 787-789.

Friess, H., H. G. Beger, et al. (1996). "Treatment of advanced pancreatic cancer with mistletoe: results of a pilot trial." Anticancer Res 16(2): 915-20.

Fujimoto, T. et al. (1997). "Streptococcal Preparation OK-432 is a Potent Inducer of IL-12 and a T Helper Cell 1 Dominant State." The Journal of Immunology, vol. 158, No. 12: pp. 5619-5626.

Fujisao, S. et al. (1998). "Th1/Th2 balance alteration in the clinical course of a patient with pure red cell aplasia and thymoma." British Journal of Haematology, vol. 103, No. 2: pp. 308-310.

Gabrilovich, D. I. et al. (1996). "Dendritic Cells in Antitumor Immune Responses. II. Dendritic Cells Grown from Bone Marrow Precursors, but Not Mature DC from Tumor-Bearing Mice, Are Effective Antigen Carriers in the Therapy of Established Tumors." Cellular Immunology, vol. 170, No. 1: pp. 111-119.

Gale, R. P. et al. (1984). "How Does Bone-Marrow Transplantation Cure Leukaemia?" The Lancet, vol. 2, No. 8393: pp. 28-30.

Garlie, N.K., A.V. LeFever, et al. (1999). "T cells coactivated with immobilized anti-CD3 and anti-CD28 as potential immunotherapy for cancer." J Immunother 22(4): 336-45.

Summons to attend oral proceedings issued in related European Application No. 05724065.7 dated May 3, 2016.

Yashiro-Ohtani, Y. et al. (2000). "Non-CD28 Costimulatory Molecules Present in T Cell Rafts Induce T Cell Costimulation by Enhancing the Association of TCR with Rafts." The Journal of Immunology, vol. 164, No. 3: pp. 1251-1259.

Yoon, T. J. et al. (1998). "Prophylactic effect of Korean mistletoe (*Viscum album coloratum*) extract on tumor metastasis is mediated by enhancement of NK cell activity." International Journal of Immunopharmacology, vol. 20, No. 4-5: pp. 163-172.

Zitvogel, L. et al. (1996). "Therapy of Murine Tumors with Tumor Peptide-Pulsed Dendritic Cells: Dependence on T Cells, B7 Costimulation, and T Helper Cell 1-associated Cytokines." Journal of Experimentive Medicine, vol. 183, No. 1: pp. 87-97.

Cochlovius, et al. (2003). "Therapeutic Antibodies After Years of Promise, Magic Bullets Appear to be on the Upswing", Modern Drug Discovery, pp. 33-38.

Groth, et al. (2004). "T Cell Activation: In Vivo Veritas", Immunology and Cell Biology, vol. 82, pp. 260-268.

Japanese Office Action in corresponding Japanese Patent Application No. 2010-232031, mailed Sep. 17, 2014.

First examination report for related Israeli Patent Application No. 223938 dated Oct. 20, 2015 citing relevant art.

Geppert, T.D. et al. (1988). "Activation of T Lymphocytes by Immobilized Monoclonal Antibodies to CD3, Regulatory Influences of Monoclonal Antibodies to Additional T Cell Surface Determinants." J. Clin. Invest., vol. 81: pp. 1497-1505.

Ghosh, P., K. L. Komschlies, et al. (1995). "Gradual loss of T-helper 1 populations in spleen of mice during progressive tumor growth." J Natl Cancer Inst 87(19): 1478-83.

Gorelik, L., A. Prokhorova, et al. (1994). "Low-dose melphalan-induced shift in the production of a Th2-type cytokine to a Th1-type cytokine in mice bearing a large MOPC-315 tumor." Cancer Immunol Immunother 39(2): 117-26.

Grakoui, A. et al. (1999). "The Immunological Synapse: A Molecular Machine Controlling T Cell Activation." Science, vol. 285, No. 5425: pp. 221-227.

Granucci, F. et al. (2001). "Transcriptional reprogramming of dendritic cells by differentiation stimuli." Eur J Immunol, vol. 31, No. 9: pp. 2539-2546.

Grigg, A., P. Bardy, et al. (1999). "Fludarabine-based non-myeloablative chemotherapy followed by infusion of HLA-identical stem cells for relapsed leukaemia and lymphoma." Bone Marrow Transplant 23(2): 107-10.

Grohmann, U., M. C. Fioretti, et al. (1998). "Dendritic cells, interleukin 12, and CD4+ lymphocytes in the initiation of class I-restricted reactivity to a tumor/self peptide." Crit Rev Immunol 18(1-2): 87-98.

Hara, I., H. Hotta, et al. (1996). "Rejection of mouse renal cell carcinoma elicited by local secretion of interleukin-2." Jpn J Cancer Res 87(7): 724-9.

Heine, G. et al. (2002). "A shift in the Th(1)/Th(2) ratio accompanies the clinical remission of systemic lupus erythematosus in patients with end-stage renal disease." Nephrology Dialysis Transplantion, vol. 17, No. 10: pp. 1790-1794.

Heniford, B. T. et al. (1994). "Interleukin-8 Suppresses the Toxicity and Antitumor Effect of Interleukin-2." Journal of Surgical Research, vol. 56, No. 1: pp. 82-88.

Herlyn, D. and B. Birebent (1999). "Advances in cancer vaccine development." Ann Med 31(1): 66-78.

Horiguchi, S. et al. (1999). "Primary Chemically Induced Tumors Induce Profound Immunosuppression Concomitant with Apoptosis and Alterations in Signal Transduction in T Cells and NK Cells." Cancer Research, vol. 59, No. 12: pp. 2950-2956.

Inagawa, H., T. Nishizawa, et al. (1998). "Mechanisms by which chemotherapeutic agents augment the antitumor effects of tumor necrosis factor: involvement of the pattern shift of cytokines from Th2 to Th1 in tumor lesions." Anticancer Res 18(5D): 3957-64.

Ito, N. et al. (1999). "Lung Carcinoma: Analysis of T Helper Type 1 and 2 Cells and T Cytotoxic Type 1 and 2 Cells by Intracellular Cytokine Detection with Flow Cytometry." Cancer, vol. 85, No. 11: pp. 2359-2367.

Janes, P. W. et al. (1999). "Aggregation of Lipid Rafts Accompanies Signaling Via the T Cell Antigen Receptor." The Journal of Cell Biology, vol. 147, No. 2: pp. 447-461.

Jung, U. et al. (Nov. 2003). "CD3/CD28-costimulated T1 and T2 subsets: differential in vivo allosensitization generates distinct GVT and GVHD effects." Blood, vol. 1, No. 9: pp. 3439-3446.

(56) References Cited

OTHER PUBLICATIONS

Kadowaki, N. et al. (2002). "Natural Type I Interferon-Producing Cells as a Link Between Innate and Adaptive Immunity." Human Immunology, vol. 63, No. 12: pp. 1126-1132.
Kai, S. and H. Hara (2003). "Allogeneic hematopoietic stem cell transplantation." Therap Apher Dial 7(3): 285-91.
Kasakura, S. (1998). "[A role for T-helper type 1 and type 2 cytokines in the pathogenesis of various human diseases]." Rinsho Byori 46(9): 915-21.
Kitahara, S., M. Ikeda, et al. (1996). "Inhibition of head and neck metastatic and/or recurrent cancer by local administration of multi-cytokine inducer OK-432." J Laryngol Otol 110(5): 449-53.
Knoefel, B., K. Nuske, et al. (1997). "Renal cell carcinomas produce IL-6, IL-10, IL-11, and TGF-beta 1 in primary cultures and modulate T lymphocyte blast transformation." J Interferon Cytokine Res 17(2): 95-102.
Kobayashi, M. et al. (1998). "A Pathogenic Role of Th2 Cells and Their Cytokine Products on the Pulmonary Metastasis of Murine B16 Melanoma." The Journal of Immunology, vol. 160, No. 12: pp. 5869-5873.
Kobayashi, M., R. B. Pollard, et al. (1997). "Inhibition of pulmonary metastasis by Z-100, an immunomodulatory lipid-arabinomannan extracted from Mycobacterium tuberculosis, in mice inoculated with B16 melanoma." Anticancer Drugs 8(2): 156-63.
Lahn, M. et al. (1999). "Pro-Inflammatory and T Cell Inhibitory Cytokines Are Secreted at High Levels in Tumor Cell Cultures of Human Renal Cell Carcinoma." European Urology, vol. 35, No. 1: pp. 70-80.
Langenkamp, A. et al. (2000). "Kinetics of dendritic cell activation: impact on priming of TH1, TH2 and nonpolarized T cells." Nature Immunology, vol. 1, No. 4: 311-316.
Laux, I. et al. (2000). "Response Differences between Human CD4(+) and CD8(+) T-Cells during CD28 Costimulation: Implications for Immune Cell-Based Therapies and Studies Related to the Expansion of Double-Positive T-Cells during Aging." Clinical Immunology, vol. 96, No. 3: pp. 187-197.
Le Bon, A. et al. (2002). "Links between innate and adaptive immunity via type I interferon." Current Opinion Immunology, vol. 14, No. 4: pp. 432-436.
Lee, P. P. et al. (1997). "T Helper 2-Dominant Antilymphoma Immune Response Is Associated With Fatal Outcome." Blood, vol. 90, No. 4: pp. 1611-1617.
Levine, B.L. et al. (1997). "Effects of CD28 Costimulation on Long-Term Proliferation of CD4+ T Cells in the Absence of Exogenous Feeder Cells." The Journal of Immunology, vol. 159, No. 12: pp. 5921-5930.
Li, L. et al. (1998). "Cyclophosphamide Given After Active Specific Immunization Augments Antitumor Immunity by Modulation of Th1 Commitment of CD4+ T Cells." Journal of Surgical Oncology, vol. 67, No. 4: pp. 221-227.
Liebowitz, D.N. et al. (1998). "Costimulatory approaches to adoptive immunotherapy." Current Opinion Oncology, vol. 10, No. 6: pp. 533-541.
Lowes, M. A., G. A. Bishop, et al. (1997). "T helper 1 cytokine mRNA is increased in spontaneously regressing primary melanomas." J Invest Dermatol 108(6): 914-9.
Ludviksson, B. R. et al. (2000). "The effect of TGF-β1 on immune responses of naive versus memory CD4+ Th1/Th2 T cells." Eur J Immunol, vol. 30, No. 7: pp. 2101-2011.
Lum, L.G. et al (2001). "Immune modulation in cancer patients after adoptive transfer of ani-CD3/anti-CD28- costimulated T-cells—phase I clinical trial." Journal of Immunotherapy, vol. 24, No. 5: pp. 408-419.
Ma, J. et al. (1998). "Use of encapsulated single chain antibodies for induction of anti-idiotypic humoral and cellular immune responses." Journal of Pharmaceutical Sciences, Vo. 87, No. 11: pp. 1375-1378.
Maeurer, M. J., D. M. Martin, et al. (1995). "Host immune response in renal cell cancer: interleukin-4 (IL-4) and IL-10 mRNA are frequently detected in freshly collected tumor-infiltrating lymphocytes." Cancer Immunol Immunother 41(2): 111-21.
Maus, M. V. et al. (2002). "Ex vivo expansion of polyclonal and antigen-specific cytotoxic T lymphocytes by artificial APCs expressing ligands for the T-cell receptor, CD28 and 4-1BB." Nature Biotechnology, vol. 20, No. 2: pp. 143-148.
Menetrier-Caux, C. et al. (1999). "Renal cell carcinoma induces interleukin 10 and prostaglandin E2 production by monocytes." British Journal of Cancer, vol. 79, No. 1: pp. 119-130.
Moran, M. et al. (1998). "Engagement of GPI-Linked CD48 Contributes to TCR Signals and Cytoskeletal Reorganization: A Role for Lipid Rafts in T Cell Activation." Immunity, vol. 9, No. 6: pp. 787-796.
Muller, M. et al. (2003). "Surface modification of PLGA microspheres." Journal of Biomedic Material Research, vol. 66A, No. 1: pp. 55-61.
Nabioullin, R. et al. (1994). "Interleukin-10 is a potent inhibitor of tumor cytotoxicity by human monocytes and alveolar macrophages." Journal of Leukocyte Biology, vol. 55, No. 4: pp. 437-442.
Nakagomi, H. et al. (1995). "Lack of Interleukin-2 (IL-2) Expression and Selective Expression of IL-10 mRNA in Human Renal Cell Carcinoma." Int. Journal of Cancer, vol. 63, No. 3: pp. 366-371.
Nishimura, T. et al. (2000). "The critical role of Th1-dominant immunity in tumor immunology." Cancer Chemother Pharmacol, vol. 46 (Supply): S52-S61.
Nitta, T., M. Hishii, et al. (1994). "Selective expression of interleukin-10 gene within glioblastoma multiforme." Brain Res 649(1-2): 122-8.
O'Donnell P.B. et al. (1997). "Preparation of microspheres by the solvent evaporation technique." Advanced Drug Delivery Reviews, vol. 28, No. 1: pp. 25-42.
Oka, H. et al. (1999). "An immunomodulatory arabinomannan extracted from Mycobacterium tuberculosis, Z-100, restores the balance of Th1/Th2 cell responses in tumor bearing mice." Immunology Letters, vol. 70, No. 2: pp. 109-117.
Okamoto, T. et al. (1997). "Local Injection of OK432 Can Augment the TH1-Type T-Cell Response in Tumor-Draining Lymph Node Cells and Increase Their Immunotherapeutical Potential." International Journal of Cancer, vol. 70, No. 5: pp. 598-605.
Okutomi, T., Y. Kato, et al. (2000). "[Clinical effects of adjuvant therapy using Z-100 (Ancer 20 injection) for oral cancer—prevention of stomatitis and hematopoietic impairment]." Gan to Kagaku Ryoho 27(1): 65-71.
Onishi, T. et al. (1999). "An assessment of the immunological environment based on intratumoral cytokine production in renal cell carcinoma." BJU International, vol. 83, No. 4: pp. 488-492.
Raghupathy, R. (1997). "Th1-type immunity is incompatible with successful pregnancy." Immunology Today, vol. 18, No. 10: pp. 478-482.
Office Action issued for related Japanese patent application No. 2016-152801, dated May 1, 2017. (English machine translation included).

METHOD FOR ALLOGENEIC CELL THERAPY

CROSS-REFERENCE TO RELATED APPLICATION

The present application is a divisional of and claims priority to U.S. patent application Ser. No. 14/173,494, filed Feb. 5, 2014, which is a divisional of and claims priority to U.S. patent application Ser. No. 13/596,142, filed Aug. 28, 2012, now U.S. Pat. No. 8,679,841, which is a divisional of and claims priority of U.S. patent application Ser. No. 12/869,490, filed Aug. 26, 2010, now U.S. Pat. No. 8,273,377, which is a continuation of and claims priority of U.S. patent application Ser. No. 12/172,594, filed Jul. 14, 2008, now U.S. Pat. No. 7,943,180, which is a divisional of U.S. patent application Ser. No. 10/838,454, filed May 4, 2004, now U.S. Pat. No. 7,435,592, which claims priority to U.S. patent application Ser. Nos. 60/549,032, filed Mar. 1, 2004, 60/547,966, filed Feb. 26, 2004, 60/545,450, filed Feb. 18, 2004, and 60/470,171, filed May 13, 2003, the contents of which are hereby incorporated by reference in their entirety.

FIELD OF INVENTION

This invention relates to the use of allogeneic cell infusions to treat disease. More particularly, the invention relates to an allogeneic cell therapy method enabling the generation of an anti-tumor effect in the absence of graft vs. host (GVH) disease toxicity.

BACKGROUND OF THE INVENTION

Allogeneic cell therapy is an important curative therapy for several types of malignancies and viral diseases. Allogeneic cell therapy involves the infusion or transplant of cells to a patient, whereby the infused or transplanted cells are derived from a donor other than the patient. Types of allogeneic donors that have been utilized for allogeneic cell therapy protocols include: HLA-matched siblings, matched unrelated donors, partially matched family member donors, related umbilical cord blood donors, and unrelated umbilical cord blood donors. The allogeneic donor cells are usually obtained by bone marrow harvest, collection of peripheral blood or collection of placental cord blood at birth. This requirement for a matched donor is a major limitation of allogeneic cell therapy protocols. It is an object of this invention to provide a method of allogeneic cell therapy that is effective without the requirement for HLA matching.

Allogeneic cell therapy methods have been practiced in the bone marrow transplant (BMT) setting for over 30 years (Kai and Hara 2003). These methods involve treatment of patients with high dose (myeloablative) chemotherapy and/or radiation. This myeloablative conditioning results in destruction of the bone marrow leading to the loss of a functioning immune system. Thus, these patients must be "rescued" by allogeneic cell transplant to replace the destroyed bone marrow and restore immunity.

The ability of myeloablative conditioning followed by allogeneic BMT or stem cell transplantation (SCT) to cure certain hematological malignancies is widely recognized. The anti-tumor effect mediated by the allogeneic cell transplant is known as the graft vs. tumor (GVT) effect (also called the graft vs. leukemia effect and the graft vs. malignancy effect and the graft vs. myeloma effect). GVT activity after allogeneic cell therapy is known to be effective in treating several cancers, including myeloid leukemias (Gale and Champlin 1984), lymphoid leukemias (Rondon, Giralt et al. 1996, multiple myeloma {Tricot, 1996 #2730) and breast cancer (Eibl, Schwaighofer et al. 1996).

However, allogeneic BMT has a treatment related mortality of 30-35% (Frassoni, Labopin et al. 1996). The high risk of transplant related mortality has limited the use of this treatment mostly to otherwise healthy patients with hematological malignancies. It is an object of this invention to significantly reduce or eliminate the treatment related mortality of allogeneic cell therapy in order to make the treatment available to a broader spectrum of patients and disease indications.

The GVT effect was discovered when it was observed that relapse rates were significantly lower in patients that received an allogeneic BMT compared to patients that received an autologous BMT. This led to the discovery that the reduced relapse rate was mediated by anti-tumor reactions of lymphocytes contained in the allograft (GVT effect) (Weiden, Sullivan et al. 1981).

Direct evidence of the power of the GVT effect was first provided when patients with chronic myelogenous leukemia (CML) who relapsed after allogeneic BMT were put in complete remission after an infusion of allogeneic lymphocytes (a procedure known as Donor Lymphocyte Infusion or DLI). DLI treatment has since been shown to frequently cause complete remissions in relapsed cancer patients following allogeneic BMT, despite complete resistance of such tumor cells to maximally tolerated doses of chemotherapy/radiation (Slavin, Naparstek et al. 1995; Slavin, Naparstek et al. 1996; Slavin, Naparstek et al. 1996) (See also Slavin U.S. Pat. Nos. 5,843,435 and 6,143,292).

The observation that DLI treatment alone, without chemotherapy, could have an anti-tumor effect has led to a paradigm shift in the treatment of malignancy A new generation of therapies has emerged where the focus is on the GVT effect, rather than the cytotoxic effect of chemotherapy/radiation. This new generation of allogeneic cell therapy protocols is known as a "Mini-Transplant" (for example, see U.S. Pat. No. 6,544,787 issued to Slavin and U.S. Pat. No. 6,558,662 issued to Sykes, et al.).

Mini-Transplant procedures involve a first round of low dose, non-myeloablative chemotherapy conditioning of a patient. The low dose chemotherapy conditioning is not provided for the purpose of tumor reduction, but rather is designed to only weaken the immune system enough to prevent rejection of an allogeneic donor cell infusion. Conditioned patients are infused with non-manipulated allogeneic lymphocytes or stem cells which engraft in the patients and subsequently mediate a GVT effect.

Patients with successfully engrafted allogeneic cells develop immune systems which are partially of self origin and partially of the allogeneic graft origin. Patients in this immunological state are known as "chimeras". The conditioning regimen enabling chimera formation usually includes administration of one or more chemotherapy conditioning agents, such as purine analogs like fludarabine, alkylating agents such as busulfan and/or cyclophosphamide, and/or anti-leukocyte globulins (see U.S. Pat. No. 6,544,787 issued to Slavin).

These Mini-Transplant protocols have proven to be very effective in the treatment of hematological malignancies and are less toxic than the high dose myeloablative regimens (Champlin, Khouri et al. 1999; Champlin, van Besien et al. 2000); (Grigg, Bardy et al. 1999); (Slavin, Nagler et al. 2001; Slavin, Or et al. 2001). Mini-Transplants have also been shown to be effective in chemotherapy resistant metastatic disease (Childs, Chernoff et al. 2000; Childs 2000; Childs and Barrett 2002; Childs 2002).

While the GVT effect has been described as the most powerful and effective anti-tumor mechanism ever observed in the treatment of human malignancies (van Besien, Thall et al. 1997) (Eibl, Schwaighofer et al. 1996) (Ueno, Rondon et al. 1998), the clinical application of GVT is still severely limited due to the toxicity associated with allogeneic cell infusions. The major complication of allogeneic cell therapy is the condition known as graft vs. host (GVH) disease. GVH disease occurs when donor T-cells react against antigens on normal host cells causing target organ damage, which often leads to death. The principal target organs of GVH disease are the immune system, skin, liver and intestine.

There is an urgent need to develop methods to separate the beneficial GVT effect from the detrimental GVH effect in allogeneic cell therapy. However, this has proven to be very difficult, as it appears that GVT and GVH are intimately related processes, with the same donor T-cells responsible for both effects. It is an object of this invention to describe an allogeneic cell therapy method which provides an anti-tumor effect without the toxicity associated with GVH disease.

GVH disease occurs secondary to mismatches between histocompatibility antigens (HLA) between the donor and the recipient. Attempts to perform allogeneic BMT between strongly HLA-mismatched donor-recipient pairs have been associated with a prohibitively high incidence of severe GVH disease and failure of the allogeneic cell infusions to engraft. Therefore, allogeneic cell therapy normally requires matching of HLA antigens between donor and recipient. However despite matching of HLA identity, substantial numbers of patients still develop GVH disease, presumably due to differences in minor HLA antigens.

The requirement for an HLA matched donor severely limits the application of allogeneic cell therapy. Only approximately one of every three patients has an HLA-matched sibling or can find a phenotypically matched unrelated donor, and therefore the majority of patients do not have the option of allogeneic cell therapy. Furthermore, a large fraction of cancers, including leukemias and lymphomas, afflict older patients who are more prone to the development of GVH disease than are younger persons, and who therefore are not generally considered candidates for allogeneic cell therapy, despite the lack of other curative options. In addition, the immunosuppressive drugs used for GVH disease prophylaxis also increase the risk of secondary infection and increase the relapse rates for certain types of leukemia.

Accordingly, there is a great need to reduce or eliminate the toxicity associated with GVH disease in allogeneic cell therapy protocols while maintaining or increasing the GVT effect in order that the therapy could be utilized to benefit a greater population of patients.

It is an object of this invention to describe an allogeneic cell therapy method that elicits an anti-tumor effect at least as effective as the GVT effect without the associated GVH disease toxicity.

It is an additional object of this invention to describe an allogeneic cell therapy method with reduced treatment related toxicity by eliminating the requirement for a previous allogeneic BMT or chemotherapy conditioning regimen in order to benefit from the therapy.

It is an additional object of this invention to describe a method of allogeneic cell therapy that does not require an HLA-matched donor.

SUMMARY OF THE INVENTION

The invention disclosed herein relates to a product comprised of allogeneic cells of which at least a portion are T-cells, whereby the allogeneic T-cells are expanded and differentiated ex-vivo, and are used as an allogeneic cell therapy for the stimulation of the host immune system in humans without GVH toxicity, and whereby said allogeneic cells are subsequently rejected by the host immune system.

The invention disclosed herein also relates to a product described above whereby the allogeneic cells are chosen without regard for HLA-match with the recipient, or to allow for the maximum mismatch of HLA haplotype with the intended patient population, thereby ensuring the maximum allogeneic potential and subsequent host immune response to the product.

The invention disclosed herein also relates to a product described above whereby the allogeneic cells are capable of stimulating an effective host immune response against a tumor when infused into patients that have not received a prior allogeneic BMT.

The invention disclosed herein also relates to a product described above whereby the allogeneic cells are capable of stimulating an effective host immune response against a tumor when infused into a patient that has not been subjected to immunosuppressive conditioning regimens.

The invention disclosed herein also relates to a product described above whereby the allogeneic cell therapy stimulates an immune response in patients by stimulating the production of inflammatory "Type 1" monokines and lymphokines in the host.

The invention disclosed herein also relates to a product described above whereby the allogeneic cell therapy stimulates an immune response in patients by activating components of host innate and/or Th1 adaptive immunity.

The invention disclosed herein also relates to a product described above whereby the allogeneic cell therapy stimulates the production of cytokines which enhance the immunogenicity of tumors.

The invention disclosed herein also relates to a product described above whereby the allogeneic cells directly kill tumors so as to cause the tumor associated antigens to be available for stimulating host Type 1 adaptive immunity.

The invention disclosed herein also relates to a method of producing a product as described above, whereby the allogeneic T-cells contained in the product are in a state of enhanced activation.

The invention disclosed herein also relates to a method for stimulating a host immune system by collecting the mononuclear cells from an unrelated donor, activating T-cells within the mononuclear cell population, and administering the activated T-cells to a host having a host immune system whereby the activated T-cells are rejected by the host immune system while stimulating the host immune system to mediate an effective immune response against a resident disease. The host may have a resident disease such as hematological malignancy, a solid tumor, a solid tumor that has metastasized or a viral infection. The donor is selected without regard to histocompatibility to the host, and maximum histocompatibility mismatch is preferred. The host also preferably should not have had a prior bone marrow transplant and should not preferably have received any immunosuppressive chemotherapy and/or radiation conditioning regimens designed to allow engraftment of the allogeneic donor cell infusions.

The method further includes that the T-cells are preferably CD4+ T-cells and that a majority of the CD4+ T-cells differentiate after ex-vivo activation from CD45RA+, CD62L$^{hi}$ naïve cells into CD45RO+, CD62L$^{lo}$ memory cells, and wherein such cells produce Type 1 cytokines such as IL-2, IFN-gamma, TNF-alpha and do not produce Type 2 cytokines such as IL-4, IL-10 and TGF-beta.

The invention disclosed herein also includes such CD4+ T-cells which after ex-vivo activation express CD40L and/or TRAIL on the cell surface.

Preferably, the T-cells are activated by cross-linking of anti-CD3 and anti-CD28 mAbs applied to the cell surface of the T-cells. Preferably anti-CD3 and anti-CD28 mAbs applied to the surface of said T-cells are cross-linked by association with biodegradable microspheres coated with an agent reactive against said mAbs.

The invention disclosed herein also includes wherein greater than 90% of the T-cells are in a state of activation just prior to and at the time of contacting the host immune system, and in the preferred embodiment greater than 95% of the T-cells are activated at the time of administration to the host and just prior to contacting the host.

The method also includes wherein T-cells are continuously exposed to an activating stimulus for at least six days prior to infusion in the host. T-cells are preferably activated while being maintained at cell densities of at least $10^7$ cells/ml to maximize cell to cell contact. Such cell to cell contact serves to enhance the state of activation of the allogeneic T-cells.

In another embodiment, the method includes wherein the T-cells are administered with anti-CD3 and anti-CD28 mAbs applied to the surface of the allogeneic T-cells and wherein the mAbs are cross-linked by association with and inclusion of biodegradable microspheres coated with an agent reactive against the mAbs.

The method also includes wherein T-cell administration stimulates production of Type 1 cytokines, and such cytokines include at least one of the following: IL-1, IL-2, IL-12, IL-15, IFN-gamma, IFN-alpha, IFN-beta, TNF-alpha, and TNF-beta. Such cytokines stimulate immunity including host innate immune function. The method also includes wherein the activated T-cell administration activates host dendritic and/or macrophage cells.

The invention also includes wherein the activated allogeneic T-cell administration and subsequent rejection of the activated T-cells stimulates an immune response against a host resident disease.

The invention also includes a method wherein the ex-vivo activated allogeneic T-cells are cryopreserved prior to formulation and administration to the host.

The invention also includes a composition of allogeneic T-cells labeled with anti-CD3 and anti-CD28 mAbs cross-linked with biodegradable microspheres coated with an agent reactive against said mAbs. The labeled allogeneic T-cells and associated biodegradable microspheres are suspended in a media suitable for intravenous infusion. Such T-cells and associated biodegradable microspheres are suspended at a cell density of $10^7$ cells/ml or greater, and preferably in a flexible container or in a syringe. The T-cells labeled with anti-CD3 and anti-CD28 may also be cryopreserved prior to formulation and administration.

The present invention also includes an allogeneic cell material that elicits a host vs. tumor (HVT) and host vs. graft (HVG) response when contacted with a tumor-bearing host immune system without eliciting a toxic graft vs. host (GVH) response. The allogeneic cell material contains ex-vivo activated T-cells and wherein said activated T-cells are preferably CD4+ T-cells.

The present invention also includes an allogeneic cell material that causes apoptosis of tumors when administered to a tumor-bearing host. The allogeneic cell material contains activated allogeneic T-cells, and such T-cells are preferably CD4+ cells. Such CD4+ cells should express FasL and/or TRAIL on the cell surface, preferably at high density. Such activated T-cells preferably differentiate into memory cells expressing CD45RO and CD63L$^{lo}$ after ex-vivo activation. Such allogeneic T-cells should express one or more of the following cytokines: IL-2, IL-15, IFN-gamma, and TNF-alpha and express surface FasL and/or TRAIL upon administration to the host.

The present invention also includes a composition comprising a treatment effective amount of a population of allogeneic cells, of which at least a portion are T-cells, and whereby said T-cells are labeled with an activating effective amount of one or more monoclonal antibodies, or portions thereof, and a cross-linking effective amount of an agent reactive against the monoclonal antibodies. T-cells of such composition are preferably labeled with anti-CD3 and anti-CD28 mAbs. The agent reactive against the mAbs is preferably coated on biodegradable microspheres. The allogeneic T-cells and associated biodegradable microspheres are suspended in a media suitable for intravenous infusion. Such labeled T-cells and associated cross-linking biodegradable microspheres are suspended at a cell density of $10^7$ cells/ml or greater in a flexible container or in a syringe. The composition may be cryopreserved prior to infusion.

In preferred embodiments, the allogeneic cells used in the present invention are purified T-cells which have been activated ex-vivo, preferably CD4+ T-cells, more preferably CD4+ T-cells that have differentiated into effector or memory cells and produce high levels of Type 1 cytokines, such as IL-2, IL-15, IFN-gamma, TNF-alpha and also express, preferably at high density, effector molecules such as CD40L, TRAIL and FasL on the cell surface.

In another preferred embodiment, the allogeneic T-cells for infusion are processed ex-vivo by a method which maintains the cells at high cell density ($10^7$ cells/ml or greater) in continuous contact with T-cell activating agents.

In another preferred embodiment, the allogeneic T-cells for infusion are formulated in media suitable for infusion containing activating agents as a means to maintain the activation state of the T-cells from harvest through infusion.

In another preferred embodiment, greater than 90%, or preferably greater than 95% of the infused allogeneic T-cells continue in a state of enhanced activation at the time of infusion into the patient.

The "Mirror Effect"

In the prior art allogeneic cell therapy protocols, T-cells in the graft are responsible for mediating the beneficial GVT effect and the detrimental GVH effect of the therapy. In order to accomplish the objectives of this invention, a new mechanism is described whereby the T-cells in the graft do not directly mediate the immune effects, but instead act to stimulate the host immune system to mediate an effective immune response against a resident disease.

The host immune response elicited by the method of this invention is the "mirror" of the GVT/GVH effects of prior art allogeneic cell therapy protocols. The "mirror" of the normally observed GVT effect in allogeneic cell therapy is the host vs. tumor (HVT) effect. The "mirror" of the normally observed GVH effect in allogeneic cell therapy is the host vs. graft (HVG) effect. The HVT/HVG effects are hereinafter collectively called the "Mirror Effect".

Unlike the extremely toxic GVH component of prior art allogeneic cell therapy protocols, the HVG component of the Mirror Effect results only in the non-toxic rejection of the graft cells. Thus in the present invention, the HVT anti-tumor component of the Mirror Effect occurs without the toxicity of GVH. It is understood in the art that an effective anti-tumor immune response can also be effective against a variety of pathogens, including viruses.

In the present invention, the rejection of the graft (HVG) is a desired component of the Mirror Effect. Therefore, it is not necessary to treat the recipient patients with immunosuppressive conditioning regimens in order to prevent rejection of the graft, as is required in prior art allogeneic cell therapy protocols. In addition, unlike the GVH component of prior art allogeneic cell therapies, the HVG component of the Mirror Effect is a non-toxic immunological event. In prior art allogeneic cell therapy protocols it is necessary to select HLA-matched donors in order to reduce the toxic effects of the GVH effect. Since the HVG component of the Mirror Effect is non-toxic, it is not necessary to use an HLA-matched donor in the present invention as a means to limit the effect. In fact, it is preferable in the practice of the present invention to use allogeneic donors that have complete HLA disparity with the host. The greater the HLA disparity, the stronger the stimulation of the host immune response.

In prior art allogeneic cell therapy protocols the beneficial GVT effect and the detrimental GVH effect are intimately and proportionally related. There are at least two forces which serve to limit the magnitude of the GVT effect in these prior art allogeneic cell therapy protocols that are not present to limit the anti-tumor HVT component of the Mirror Effect. These factors are: (1) the development of host tolerance to the donor cells enabling engraftment and chimerism; and (2) GVH prophylaxis with immune suppressive drugs.

Host tolerance is an immune mechanism where the host immune system ceases to respond against the graft cells and the graft cells cease to respond against the host cells. The mechanism of tolerance is correlated with immunosuppressive mechanisms resulting in the undesired reduction of the GVT effect. GVH prophylaxis is required in prior art allogeneic cell therapy protocols in order to limit the extent of GVH disease. Because of the proportional relationship between GVT and GVH, the limitation of the GVH component by prophylaxis proportionally limits the GVT component.

In the Mirror Effect, the HVT and HVG components are also intimately and proportionally related. The HVT component provides a more powerful anti-tumor effect than the GVT effect. This is because the HVG effect does not require immunosuppressive treatment to limit the extent of the rejection response. In this way, unlike the GVH effect, the HVG effect can be allowed to reach its natural conclusion (complete rejection). The proportional nature of the HVG effect with the anti-tumor HVT effect results in a more powerful anti-tumor component occurring concurrently and in proportion to the rejection response. It is preferred, therefore, that the rejection response be enhanced, rather than limited, by the use of completely mis-matched allogeneic cells. The enhanced HVT anti-tumor effect also occurs because, unlike the GVT effect, the HVT effect does not occur in the limiting environment of tolerance induction. In the present invention, rather than an immunosuppressive tolerance effect, a powerful Th1-mediated allo-rejection response is mediated. This Th1 allo-rejection response has a by-stander effect which helps to sustain and amplify the HVT effect.

Accordingly, the allogeneic cell therapy of the present invention provides significant advantages for the treatment of malignancies over prior art methods: (1) enhanced anti-tumor effect (HVT) compared to the GVT effect; (2) potentially curative anti-tumor effect without lethal toxicity; (3) elimination of the requirement for a matched donor; (4) elimination of the need for immunosuppressive conditioning prior to therapy; and (5) elimination of the need for a prior allogeneic BMT (as is required in DLI protocols).

Ex-Vivo Manipulation Requirement

In order for a population of allogeneic cells to induce the Mirror Effect, the population must contain T-cells. To be effective, the allogeneic T-cells must be manipulated ex-vivo in a manner that causes activation. The T-cells need not be activated with specific antigens, but preferably are activated polyclonally Preferably the activated T-cells proliferate at least 4 generations and differentiation to obtain effector function. T-cells that express effector function produce Type 1 cytokines including IL-2, IFN-gamma and TNF-alpha, express activation markers such as CD25 and HLA-DR, and express effector molecules such as TNF superfamily molecules such as TRAIL, LIGHT, CD40L and FasL. In another preferred embodiment, the ex-vivo activated allogeneic T-cells further differentiate into memory cells that express CD45RO and CD62L$^{lo}$.

T-cells generally require two signals to be activated. The first signal required for activation occurs by stimulation of the T-cell antigen receptor (TCR), a multisubunit immune recognition receptor that associates with the CD3 complex and binds to peptides presented by the major histocompatibility complex (MHC) class I (CD8+ T-cells) and class II (CD4+ T-cells) proteins on the surface of antigen-presenting cells (APCs). The first signal can be provided by immobilized anti-CD3 mAb. The second signal is typically delivered through co-stimulatory molecules. The major co-stimulatory signal occurs when a member of the B7 family ligands CD80 or CD86 on an activated antigen-presenting cell (APC) binds to CD28 on a T-cell. The second signal can be provided by soluble or immobilized anti-CD28 mAb. For purposes herein, T-cells at a cell density of less than $10^6$ cells per ml and activated with anti-CD3 and anti-CD28 are termed "standard conditions".

In the present invention, the T-cells should enter and maintain a state of "enhanced activation" prior to infusion. For purposes of the present invention, "enhanced activation" shall mean a T-cell that has been activated in a manner that results in enhanced proliferation characteristics (i.e., proliferation greater than a population activated under standard conditions) and terminally differentiates to perform enhanced effector functions, including enhanced cytokine production and enhanced expression of effector molecules when compared to T-cells activated under standard conditions.

In a preferred embodiment, a population of allogeneic T-cells with enhanced activation characteristics are produced by a process that involves: (1) collection of mononuclear cells by leukapheresis; (2) purification of CD4+ cells from the mononuclear cells; (3) contacting the CD4 cells with cross-linked anti-CD3 and anti-CD28 mAbs; (4) maintaining constant contact of the cross-linked CD3/CD28 mAbs on the CD4 cells for at least a period of 6 days; (5) maintaining over the same minimum 6 day period enhanced cell to cell contact; and (6) formulating and then infusing the CD4 cells at the peak of proliferation and cytokine production while maintaining constant contact with the cross-linked CD3/CD28 mAbs.

Prior art allogeneic cell therapies generally involve infusion of non-manipulated allogeneic cells into a host with an immune system that has been suppressed by chemotherapy and/or radiation conditioning regimens. These prior art procedures result in engraftment of the allogeneic cells, which in turn mediate the GVT/GVH effects. Ex-vivo manipulation of the graft cells in this setting may increase GVT effects, but also results in exacerbation of the toxic GVH effects. Infusion of non-manipulated allogeneic cells into a host with an intact immune system results only in rejection of the allogeneic cells (HVG) without any anti-tumor effect. Therefore, the manipulation of the allogeneic graft cells is a required embodiment for eliciting the Mirror Effect.

The present invention is designed to take advantage of the known mechanisms of the GVT effect in prior art allogeneic cell therapy protocols, including the key role of the innate immune system in initiating effective, appropriate and targeted adaptive immune responses and the role Type 1 cytokines have in bridging innate and adaptive immunity. The method of the present invention is designed to mirror the known mechanisms that mediate the GVT effect within the host (rather than within the graft).

Patients with tumors have immune responses that have failed to protect against the tumor. This can be for many reasons, including the initial imprinting of a Type 2 immune response against the tumor and/or due to tumor immunoavoidance mechanisms. The GVT effect of prior art allogeneic cell therapy protocols is capable of overcoming these limitations in some settings. The key to overcoming these limitations is the stimulation of an inflammatory Type 1 cytokine storm (described in more detail below) in the context of de novo shedding of tumor antigen resulting from the conditioning regimens, as well as the activation of components of innate immunity in the graft and the subsequent imprinting of a de novo graft-mediated Type 1 adaptive immune response against the tumor.

The present invention is designed to elicit these mechanisms in the host rather than the graft. Accordingly, the allogeneic cells of the present invention are designed to elicit a Type 1 cytokine storm, de novo shedding of tumor antigen, activation of components of host innate immunity leading to a host Type 1 adaptive immune response against the tumor.

The major cellular components of the innate immune system consists of macrophages, NK cells, neutrophils, gamma-delta T-cells, alpha-beta intermediate T-cells and NKT cells. The activation of the host innate immune response to tumors results in the killing of tumors, shedding of tumor associated antigens (TAA) into draining lymph nodes, enhanced presentation of TAA to naïve T-cells and also plays an instructive role in emanating the subsequent Type 1 adaptive immune response.

Components of the adaptive immune response coordinate to specifically eliminate the tumor. The adaptive immune response is characterized by its specificity for a tumor and the ability to distinguish between self and non-self. The major cellular components of the adaptive anti-tumor immune response consist of CD4+ T-cells and CD8+ T-cells. Antigen presenting cells (APC), such as activated dendritic cells, plasmacytoid dendritic cells and macrophages serve to bridge between the innate and adaptive immune compartments by presenting TAA to components of the adaptive immune system.

In order to elicit the full benefit of the Mirror Effect, the allogeneic cell infusion must be manipulated ex-vivo so that the cells are capable of eliciting a cascade of immunological mechanisms upon infusion. The first mechanism the allogeneic cells should elicit is a Type 1 cytokine storm consisting of both monokines and lymphokines. In the presence of this cytokine storm, the following mechanisms should also be elicited: (1) the activation of dendritic cells; (2) the shedding of TAA; and (3) development of a Type 1 adaptive immune response.

Type 1 Cytokine Storm

Two helper (CD4) T-cell subsets, Th1 and Th2, have been defined which are characterized by distinct and mutually exclusive patterns of cytokine production. Th1 cells produce IL-2, IFN-gamma and TNF-alpha and are responsible for inducing inflammatory, cell-mediated immune responses that are protective against tumors, intracellular bacteria and viral infections. Th2 cells produce IL-4 and IL-10 and enhance humoral immune responses that are generally effective against certain extracellular bacterial and parasitic infections.

It has also been discovered that other types of immune cells exhibit distinct cytokine polarity, including CD8 T-cells, NKT-cells, NK cells and dendritic cells. A typical immune response will thus have complex mixtures of effector cells and cytokines Cytokines are an important component of any immune response and the balance of cytokines in response to a tumor or pathogen is usually determinative of the type of immune response that will be generated. The type of immune response generated is determinative of whether the tumor or pathogen will be eradicated or allowed to persist.

To assist in the categorization of immune responses, they can be characterized as 'Type 1' or 'Type 2', depending on the dominant cytokine profile. Type 1 responses are dominated by inflammatory cytokines and Type 2 responses are dominated by cytokines which suppress cellular immunity. Cytokines have been categorized as being characteristic of Type 1 or Type 2 immune responses. The cytokines are defined functionally as Type 1 or Type 2, corresponding to their ability to support cellular immunity and suppress humoral immunity (Type 1) or support humoral immunity and suppress cellular immunity (Type 2). Type 1 cytokines include IL-2, IL-12, IL-15, IFN-gamma, IFN-alpha and IFN-beta. Type 2 cytokines include IL-4, IL-5, IL-6, IL-10, IL-13 and TGF-beta. (Belardelli and Ferrantini 2002). In the case of tumors, a Type 1 immune response is critical for protective immunity (Nishimura, Nakui et al. 2000).

A common mechanism for the prior art GVT and GVH effects is a "cytokine storm" of Type 1 cytokines (Fowler, Breglio et al. 1996; Das, Imoto et al. 2001); (Carayol, Bourhis et al. 1997; Tanaka, Imamura et al. 1997; Blazar, Taylor et al. 1998; Flanagan, Jennings et al. 1999; Fowler and Gress 2000). The Type 1 cytokine storm activates components of both the innate and adaptive immune responses in the donor lymphocyte population (Antin and Ferrara 1992; Blazar, Korngold et al. 1997; Tanaka, Imamura et al. 1997). In the present invention, the infusion of the allogeneic cells is designed to elicit the same Type 1 cytokine storm. However, the present invention is designed so that the cytokine storm activates components of the innate and adaptive immune responses of the host lymphocyte population, rather than of the donor lymphocyte population. In order to assure that only host components are activated, it is preferred that the host is immunocompetent and that the allogeneic cell population infused be devoid of innate immune cells and enhanced in T-cells, preferably enhanced in CD4+ T-cells.

In preferred embodiments, the allogeneic T-cells to be infused produce high amounts of Type 1 cytokines, including IL-2, IL-15, TNF-alpha, TNF-beta, and IFN-gamma and do not produce IL-4, IL-10 or TGF-beta. The infused cells should be producing one or more of the Type 1 cytokines at the time of infusion and while circulating in the patient blood. To ensure that the allogeneic T-cells are producing Type 1 cytokines at the time of infusion and while circulating, the T-cells should be activated when infused and maintain the activation status while in circulation.

To ensure that the T-cells are activated, they should be formulated with agents which deliver activation signals. For example, the T-cells can first be contacted with activating agents, such as mouse anti-human CD3 and mouse anti-human CD28 mAbs. The mAbs on the surface of the T-cells can then be cross-linked to deliver activation signals to the T-cells. In preferred embodiments, the cross-linking is accomplished by including coated biodegradable microspheres or nanospheres in the formulation media. The biodegradable spheres are coated with an agent which reacts with the activating agents on the T-cells and causes them to be cross-linked and to deliver activation signals. Suitable coating agents for use with mouse mAbs include polyclonal anti-mouse antibodies or monoclonal anti-Fc mAbs.

The method of the present invention comprises introducing a sufficient amount of activated allogeneic T-cells, preferably CD4+ T-cells, into a host to stimulate host mononuclear cells to produce Type 1 cytokines, especially IL-1, IL-12, IL-15, IL-18, TNF-alpha, GM-CSF, IFN-alpha and IFN-gamma and not inducing significant production of IL-4, IL-10, IL-13 and TGF-beta from host cells.

The production of the Type 1 cytokine storm is known to be important in the link between the initial innate immune activation and the subsequent adaptive immune response in anti-tumor immunity (Belardelli and Ferrantini 2002; Kadowaki and Liu 2002; Le Bon and Tough 2002).

Activation of Dendritic Cells

A key cell type in bridging innate immunity to adaptive immunity is the dendritic cell (DC). Therefore, it is important for eliciting the full effectiveness of the Mirror Effect for the allogeneic cell infusion to activate host DC cells. The method of the present invention comprises introducing a sufficient amount of activated allogeneic T-cells, preferably CD4+ T-cells, into a host in order to stimulate the activation and maturation of host DCs.

After activation, DCs are known to go through maturational stages in which they express cytokines and cell surface molecules critical for the initiation and the control of innate and then adaptive immune responses (Langenkamp, Messi et al. 2000; Granucci, Vizzardelli et al. 2001). In particular, inflammatory Type 1 cytokines, such as TNF-alpha, macrophage inflammatory protein-1β (MIP-1α), IL-12 and SLAM, are strongly upregulated after activation. IL-12 is produced by monocyte-derived DCs after activation. Activated IL-12-producing DCs are then able to prime Type 1 immune responses (Langenkamp, Messi et al. 2000).

Allogeneic T-cells prepared by the process of the present invention will express CD40L (CD154) on the cell surface. These CD40L expressing T-cells will activate host DCs. Ligation of CD40 on the DCs up-regulates costimulatory/accessory molecule expression (MHC class II, CD58, CD80/CD86) that enhance antigen presentation by the DCs. This interaction in turn is known to "prime" CD40L+ helper (CD4) and cytotoxic (CD8) T cells by up-regulating their IL-2 receptor expression, and is also known to lead to the expansion of both class II□ and class I□ dependent tumor-reactive T-cell pools.

Tumor Associated Antigen (TAA) Shedding

Shedding of TAA into the draining lymph nodes and the presentation of these antigens by activated DCs stimulates an adaptive immune response. TAA shedding is caused by the killing of tumor cells by immune effector cells. In the present invention, tumor killing causing shedding of TAA is mediated by both direct and indirect mechanisms. The direct mechanism of tumor killing is mediated by the interaction of tumor cells with surface molecules on the infused allogeneic cells and/or activated host T-cells, such as FasL and TRAIL, which stimulate programmed cell death (apoptosis) of the tumor cells. The indirect mechanism includes the activation of host innate immune effector cells such as NK cells and phagocytic macrophages.

The method of the present invention comprises introducing a sufficient amount of activated allogeneic T-cells, preferably CD4+ T-cells, into a host in order to stimulate tumor lysis by elements of the innate immune system, such as NK cells. An additional method of the present invention comprises introducing a sufficient amount of activated allogeneic T-cells, preferably CD4+ T-cells, into a host which mediate tumor apoptosis through expression of TNFR effector molecules such as FasL and TRAIL. An additional method of the present invention comprises introducing a sufficient amount of activated allogeneic T-cells, preferably CD4+ T-cells, into a host which results in activation of host T-cells, whereby such activated host T-cells express TNFR ligands such as FasL and/or TRAIL and mediate apoptosis of tumor cells.

De-novo TAA shedding is an important component of the GVT effect, as it enables the reprogramming of the adaptive immune response from one that allowed tumor growth (Type 2) to one that kills and protects against the tumor (Type 1). NK cells in the graft constitute major effector cells in the GVT reaction (Voutsadakis 2003) that can mediate de-novo TAA shedding.

Similarly, activation of host NK cells is an important part of the HVT component of the Mirror Effect. The Type 1 cytokine storm, resulting from the host response to the activated allogeneic T-cells of the present invention, is capable of activating host NK cells and strongly upregulating their cytotoxic capacity:

Activated host NK cells have the ability to kill a wide variety of tumor cells spontaneously while sparing normal cells (Smyth, Hayakawa et al. 2002). Importantly, NK cells recognize potential target cells without the need for immunization or pre-activation compared with T cells, which first require education by antigen-presenting cells. Furthermore, NK cells can recognize tumors that might evade T-cell killing by down regulation of MHC I molecules, a major tumor immunoavoidance mechanism.

Therefore, the method of the current invention causes the shedding of TAA through the activation and upregulation of cytotoxic activity of host NK cells. Another mechanism for inducing the shedding of TAA by the method of the current invention is to induce apoptosis in tumors. One mechanism for the induction of apoptosis in tumors is by signaling through the death receptor called Fas (CD95). Binding of Fas with its Fas-ligand (FasL/CD154) induces programmed cell death (apoptosis). Another mechanism is by signaling through the TRAIL ligand by its counter receptor TRAIL-R. Allogeneic T-cells produced by the method of the present invention express high levels of FasL and TRAIL. However, many tumors lose expression of Fas during the tumor progression process and many tumors also express FasL as a defense against apoptosis. Approximately 80% of tumor cell lines representing colon, lung, breast, skin, kidney and brain tumors are sensitive to TRAIL induced apoptosis.

The Type 1 cytokine storm elicited by the method of the present invention upregulates the expression of Fas on tumor cells, making them susceptible to FasL-mediated apoptosis by the infused allogeneic T-cells and susceptible to a fratricide type response to other tumor cells caused by the upregulation of Fas on the FasL expressing tumor cells. In addition, the same cytokine storm activates host T-cells to express FasL which can then mediate the apoptosis of tumor cells. The same Type 1 cytokine storm also upregulates MHC I, MHC II and co-stimulatory molecules CD80 and CD86 on tumor cells, making the tumors susceptible to CTL-mediated killing in a subsequent adaptive immune response.

Type 1 Adaptive Immune Response

The method of the present invention induces the activation of host DCs and the de novo shedding of TAA in the context of a Type 1 cytokine storm. These are the conditions required for the de novo development of a host Type 1 adaptive immune response against a tumor.

The method of the present invention comprises introducing a sufficient amount of activated allogeneic T-cells, preferably CD4+ T-cells, into a host in order to stimulate a host Type 1 adaptive immune response directed against the host tumor. This mechanism is analogous to a tumor vaccine, whereby the antigen is shed by in-situ tumor killing and the Type 1 cytokine storm serves as an adjuvant for the development of the subsequent adaptive immune response. The shedding of TAA in the host and the vaccination effect of the present invention can be enhanced by the co-infusion of agents containing TAA, such as inactivated allogeneic or autologous tumors, specific TAA peptides, DNA coding TAA or cells genetically engineered to express TAA.

Some cancer patients develop a Type 1 adaptive immune response against a tumor, which fails to protect. This is known by the detection of Th1 cells in the mononuclear cell infiltrate of some progressing tumors. Therefore, the development of a Type 1 adaptive immune response alone may not be enough to have a curative effect. One of the reasons for the failure of a Type 1 adaptive immune response to protect is due to potent tumor-mediated immune avoidance mechanisms.

One method of tumor immune avoidance is by tumor-derived suppressive cytokine production. TGF-beta1 production by malignant tumors is essential for tumor progression and is one of the most important immunosuppressive cytokines secreted by tumors. Another immunosuppressive tumor-derived cytokine is IL-10. TGF-beta1 and IL-10 have been detected in tissue specimens from a variety of tumor types. TGF-beta1, and IL-10 are potent inhibitors of cellular immune function which allows tumors to escape immune surveillance and destruction by CTL.

The Type 1 cytokine storm produced by the method of the present invention causes the down regulation of tumor cell production of TGF-beta1 and IL-10. Therefore, an additional method of the present invention comprises introducing a sufficient amount of activated allogeneic T-cells, preferably CD4+ T-cells, into a host in order to down regulate tumor production of immunosuppressive cytokines such as TGF-beta1 and IL-10.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and are not intended to be limiting.

Other features and advantages of the invention will be apparent from the following detailed description.

DESCRIPTION OF THE SPECIFIC EMBODIMENTS

A preferred method for producing allogeneic cells with enhanced properties for stimulation of the Mirror Effect mechanism of the present invention involves: (1) the collection of mononuclear cell source material by leukapheresis from normal screened donors; (2) the isolation of CD4 T-cells from the source material; (3) the labeling of the CD4+ cells with anti-CD3 and anti-CD28 monoclonal antibodies (mAbs); (4) the mixing of the labeled CD4+ cells with biodegradable microspheres or nanospheres coated with an agent capable of cross-linking the mAbs on the CD4+ cells; (5) the concentration of the biodegradable spheres and labeled CD4+ cells by centrifugation; (6) the culture of the mixture in serum-free media without exogenous cytokines at cell densities in excess of $10^6$ cells/ml; (7) the culture of the cells undisturbed in an incubator for 2 days; (8) the addition of additional labeling agents and coated biodegradable spheres; (9) centrifugation of the new culture mixture followed by removal of 50-90% of the cell-free culture media volume; (10) the passage 90% of the conditioned cell-free culture media through a dialysis filter; (11) bringing the remaining 10% of the conditioned media back to the original volume with fresh culture media and adding this replenished conditioned media back to the cell mixture; (12) repeating steps 8 through 11 at least daily for a total culture period of at least 6 days.

Step 1

In practicing the preferred method provided herein, a starting population of mononuclear cells (source material) is collected from a donor, preferably by a leukapheresis procedure. The donors recruited to provide source material must be healthy and free of adventitious agents. Donors preferably will have completely mis-matched HLA antigens to the intended recipient. While not desired, source material from a partial HLA matched donor (such as a sibling of the intended recipient) can also be used in the method of the present invention. Partial matched source material need only be used if the recipient is so immunocompromised that infusion of mis-matched donor cells could cause a GVH disease reaction. Even in the case of immunocompromised individuals, it is still preferable to use mis-matched cells. In order to minimize the risk of GVH disease in these patients, the dose of the mis-matched donor cells can be reduced or the mis-matched cells could be irradiated just prior to infusion.

Generally, the donors should be carefully screened and such tests for adventitious agents conducted, as would qualify the donor to provide blood for transfusion. Examples of such tests for adventitious agents should include, at a minimum, screening for anti-HIV-1, anti-HIV-2, anti-HCV (hepatitis C), anti-HTLV-1 and anti-HTLV-2 antibodies, HbsAg (hepatitis B surface antigen), and syphilis (RPR). In a related embodiment, it is also preferable to additionally screen for CMV, and/or malaria and/or hepatitis G. Blood from any donor that tests positive for adventitious agents should not be used as source material.

Donors generally undergo an 8-12 liter leukapheresis procedure as tolerated. Donors do not need to be mobilized. The source material may be cryopreserved after collection for processing at a later date, but the material is preferably processed immediately or within 24 hours of collection. The leukapheresis source material collected should be processed by first being washed to remove plasma proteins, anticoagulant, and to reduce the number of platelets. Suitable wash media includes PBS (without calcium or magnesium) supplemented with 1-5% human serum albumen (HSA). The washing step can be performed by centrifuging the cells and removing the supernatant fluid, which is then replaced by PBS. The process can be best accomplished using a semi-automated "flow through" centrifuge (COBE 2991 System, Baxter or CytoMate, Baxter). The cells are maintained in a closed system as they are processed. Washing can be repeated up to 3 times as required. Following the wash, the WBC recovery should be greater than 85% and the platelet recovery should be less than 40%.

Step 2

The washed source material is next processed to positively select a pure population of CD4+ cells. Positive selection is preferred over negative selection techniques, as positive selection results in a known end-product and requires less reagents. The preferred method for positive selection is the use of immunomagnetic technology available from Dynal (Norway) or Miltenyi (Germany). One preferred method to positively select CD4+ cells from the source material is the use of magnetic microparticles and the CliniMACS cell separator device manufactured by Miltenyi (Germany). The cells are first labeled with anti-CD4-biotin coated monoclonal antibodies and then tagged with anti-biotin magnetic particles (supplied by Miltenyi and used in accordance with manufacturer's instructions). The solution of labeled cells is then passed over a magnetic filter for retention of the CD4 cells.

In order to maintain closed, sterile operations, the labeling of the cells in preparation for CD4 positive selection can be conducted with a CytoMate Cell Washer system (Baxter). This procedure is performed in a closed sterile disposable kit on the CytoMate device. The CliniMACS Cell Separator then uses a closed sterile disposable kit and a combination of programs and reagents to obtain an enriched population of CD4+ cells by performing an immunomagnetic positive selection on the cells tagged with the microbeads. The CLiniMACS can process a maximum of $6 \times 10^{10}$ total WBC and $5 \times 10^9$ labeled (CD4+) cells. A leukapheresis protocol normally results in the collection of approximately $10^{10}$ mononuclear cells from which approximately $10^8$ purified CD4 cells are normally collected.

Wherever possible during this procedure, a Sterile Connecting Device (Terumo) is used to make a sterile connection between bags and maintain a sterile closed system. Where use of the SCD is not possible, connections are made under strict aseptic conditions in a Laminar Flow Biosafety Cabinet.

In the positive selection of CD4+ cells, it is most important to eliminate CD8+ cells from the source material, as contaminating CD8+ cells can outgrow the CD4+ cells in subsequent steps in the process of the invention. Macrophage contamination is common after CD4+ cell positive selection. This may be due to the fact that some macrophage populations express the CD4 molecule. However, macrophages will die out in subsequent steps in the process and are not normally a great concern. Similarly, B cells will also not live through subsequent processing steps. In rare instances, macrophage contamination will cause CD4+ cell lysis or inhibition of CD4+ cell proliferation. In these cases, a macrophage reduction step prior to CD4+ cell selection might be indicated. Macrophage reduction can be accomplished by a variety of methods recognized in the art, including pre-incubation on plastic, passing through nylon wool columns or through ingestion of magnetic beads and subsequent removal in a magnetic field.

The purified CD4 cells will be mostly naïve cells with a phenotype of CD4+, CD45RA+, CD62L$^{lo}$. Contamination with up to 40% memory cells with a phenotype of CD4+, CD45RO+, CD62L$^{lo}$ will not affect the process. However, if memory cells are in excess of 40% at this step in the process, this usually indicates that the donor is not normal and thus the batch should be rejected and not used to develop cells for infusion. The purified CD4 cells can be stored at room temperature for up to 24 hours.

Step 3

The next step in the process is the ex-vivo culture of the purified CD4+ cells. It is preferred that the CD4 cells be exposed to a persistent and constant activation stimulus for at least 6 days. In order to activate the cells, they are first preferably labeled with activating agents, such as anti-CD3 and anti-CD28 mAbs and the activating agents are then cross-linked to deliver an activation signal to the CD4 cells. To label the cells, the cells are first adjusted to a cell density of $10^7$ cells per ml in serum-free culture media. A normal batch would contain around $10^8$ CD4 cells in 10 ml of media. The mAbs are each added to the cells at a final concentrations of at least 1 microgram per ml, preferably 10 micrograms per ml. The cells should be incubated with the mAbs on a rotating or end to end mixing device for 15 to 30 minutes at room temperature or preferably at 4° C. The cells should then be washed to remove excess mAbs and resuspended at $10^7$ cells per ml in serum-free culture media.

Step 4

The preferred cross-linking method is to mix the labeled cells with biodegradable nanospheres or microspheres coated with an agent reactive to the activating agents. For example, the biodegradable spheres can be coated with a mAb specific for the Fc region of the anti-CD3 and anti-CD28 mAbs, or in the case where the activating agents are mouse derived, the coating agent could be a polyclonal anti-mouse antibody. The labeled cells are mixed with the coated biodegradable microspheres at a sphere to cell ratio of at least 1:1, preferably a minimum of 3:1, and most preferably a minimum of 5:1. The sphere/cell mixture is preferably mixed well with the labeled cells for 15 to 30 minutes at room temperature, or preferably at 4° C.

Aliphatic polyesters, such as poly(lactic acid) (PLA), poly(glycolic acid) (PGA), copolymers of PLA and PGA (PLGA) or poly(carprolactone) (PCL), and polyanhydrides are preferred materials for use as biodegradable polymers for the nanospheres/microspheres. The biodegradable composition should be designed to degrade in physiological media within 7 days, more preferably within 3 days.

In a preferred embodiment of the present invention, the biodegradable spheres are constructed from a linear polyester polymer containing a mixture of lactic acid and glycolic acid. This class of polymers meets the requirements of biocompatibility and biodegradation into harmless end products for use in human biological drug preparations. These polymers, hereinafter referred to as PLGA, are degraded by ester hydrolysis into lactic acid and glycolic acid which are metabolized in the body into carbon dioxide and water. PLGA has been shown to possess excellent biocompatibility. The innocuous nature of PLGA can be exemplified by the approval by the regulatory authorities, including the U.S. Food and Drug Administration, of several parenteral delayed release preparations based on these polymers.

Copolymers of DL-lactate and glycolide, rather than L-lactate and glycolide, are preferred because they are amorphous when DL-lactate is a major component, as opposed to semicrystalline when L-lactate is a major component. This property decreases the degradation time of the polymer. The inherent viscosity (abbreviated as "I.V."; units are in deciliters/gram) of the polymer is a measure of its molecular weight. Preferably, the inherent viscosity of the polymer is from about 0.10 dL/g to about 1.0 dL/g (as measured in chloroform), more preferably from about 0.10 dL/g to about 0.50 dL/g and most preferably from 0.10 to 0.30 dL/g.

Suitable biodegradable polymer material is a 50/50 mixture of poly(DL-lactide co-glycolide). The polymer can be purchased from commercial suppliers such as Birmingham Polymers, Inc (Birmingham, Ala.) under the trade name Lactel®. The 50/50 DL-PLG product number 50DG020 with a inherent viscosity of 0.15 to 0.25 dl/g is a preferred material for use in the present invention. Another preferred material is 50/50 DL-PLG with an inherent viscosity of 0.32 to 0.44 dl/g manufactured by Boehringer Ingelheim (Ingelheim, Germany) under the trade name Resomer® RG 503. Another preferred material is Lactel® 50/50 DL-PLG product number 50D040 (Birmingham Polymers) with a 0.26 to 0.54 inherent viscosity.

Microspheres or nanospheres can be prepared by various known methods, including solvent evaporation, phase separation, spray-drying, or solvent extraction at low temperature. The process selected should be simple, reproducible and scalable. The resulting microspheres should be free-flowing and not aggregates in order to produce a uniform syringeable suspension. The microspheres must also be sterile. This can be ensured by a terminal sterilization step and/or through aseptic processing.

In a preferred embodiment, the solvent evaporation method is utilized to produce the spheres. To produce microspheres or nanospheres with this method, the hydrophobic 50/50 DL-PLG polymer is dissolved in a water-immiscible organic solvent to give a polymer solution. The solution is then added into an aqueous solution of a surfactant to form an emulsion system and stirred. The faster the stirring speed, the smaller the size of the microspheres. Microspheres are obtained by subsequently evaporating the solvent by continuous stirring, which can be under vacuum or heat.

The water-miscible organic solvents need to be non-toxic to the body. Typical examples of organic solvents are members selected from the group consisting of acetic acid, lactic acid, formic acid, acetone, acetonitrile, dimethyl formamide, dimethyl acetamide, dimethyl sulfoxide, dioxane, and N-methyl pyrrolidone and mixtures thereof. Preferably, the water-miscible organic solvent is a member selected from the group consisting of acetic acid, lactic acid, N-methyl pyrrolidone, or a mixture thereof. The water-miscible organic solvent may be used alone or in a mixture with water.

The aqueous phase can contain an emulsion stabilizer that is preferably soluble in water and alcohol, is capable of increasing viscosity of the suspending medium (water-miscible alcohol) when dissolved in the medium, is non-toxic to the body and causes no environmental problems. Typical examples of emulsion stabilizer solutions are: water-soluble synthetic polymers such as polyvinylpyrrolidone, polyethylene glycol), and poloxamer; cellulose derivatives such as hydroxypropyl cellulose and hydroxypropylmethyl cellulose, and preferably, polyvinylpyrrolidone and hydroxypropyl cellulose. The content of emulsion stabilizer in the water-miscible alcohol is preferably within the range of 0.1.to about.50% (w/v), and more preferably within the range of 0.2. to about 20% (w/v). The content of emulsion stabilizer can be varied according to the viscosity of the water-miscible alcohol needed.

The water-miscible alcohol, wherein the emulsion stabilizer is dissolved, is stirred at a temperature of 10 about.80 degrees C., preferably from 20.about.60.degree.C., and most preferably at room temperature at a speed of 200.to about.20,000 rpm, preferably at a speed of 800 to 2000 rpm. The polymer solution is slowly added to the water-miscible alcohol wherein the emulsion stabilizer is dissolved, and the mixture is stirred from 5 minutes to about.60 minutes. Stirring can be continued for up to 5 hours to allow evaporation of the organic solvent. The resulting microspheres can then collected by centrifugation and washed extensively. The washed microspheres are then ready for attachment of the cross-linking material.

The diameter of the microspheres prepared should preferably be within the range from 0.01 to 300 um, and more preferably within the range from 0.1 to 100 um. and most preferably between 0.1 and 10 um. The particle size (diameter of the microspheres) can be controlled by adjusting the stirring speed during processing, the viscosity of the water-miscible alcohol, and the viscosity of the polymer solution.

Post-coating of the biodegradable spheres with the cross-linking material can be accomplished by a variety of standard methods. In preferred embodiments, first materials that are proteins can be bond to the biodegradable microspheres by adsorption with standard known methods. A preferred method for adsorbing a protein to the biodegradable spheres is to suspend the microspheres in 0.1M Borate buffer at pH 8.5, spin down and resuspend the microspheres 2 or 3 times. The cross-linking protein, for example goat anti-mouse polyclonal antibody, is then suspended in the borate buffer at a concentration of 10 micrograms/ml and added to the microspheres at a density of $2\times10^8$ spheres per ml. The mixture is mixed end-to-end for at least 4 hours and for up to 24 hours. The mixing is preferably conducted at 4° C. After mixing, the microspheres are spun and the supernatant removed and analyzed for protein determination. The coated microspheres are then resuspended in a physiological buffer, such as phosphate buffered saline containing a blocking agent, such as 1-5% bovine or human serum albumen and/or 0.05% w/v Tween 20.

Step 5

In order to enhance the activation signals to the CD4 cells, the well mixed labeled cell/sphere mixture is spun down in a centrifuge at 500 to 800 rpm at 4° C. for 2 to 10 minutes. The force should not be so great as to tightly "pellet" the cells, but just great enough to concentrate the cells. The centrifugation forces the cells and the spheres to interact, increasing the cross-linking and the signal transduction to the CD4 cells, providing enhanced activation. The cells are preferably spun while in the gas permeable bag culture container. After centrifugation, the cells are gently resuspended by massage and agitation of the flexible bag container and placed in an incubator in an atmosphere of 5% carbon dioxide at 37° C.

Step 6

It is also preferable that the CD4 cells be kept in close cell-to-cell contact during the ex-vivo culture process. Close cell-to-cell contact can be accomplished by culturing the cells at a high cell density, preferably at $10^6$ cells per ml or greater. It is also desirable to subject the cells to frequent centrifugation in order to enhance cell-to-cell contact and the delivery of activation signals.

The purified and labeled CD4+ cells mixed with the coated biodegradable spheres should initially be suspended in culture media at a cell density of $10^6$ cells per ml and at a sphere to cell ratio of not less than 1:1, preferably greater than 3:1, and most preferably greater than 5:1. X-VIVO15 (BioWhittaker) is a preferred culture media. If the cells tend to stick to the culture containers, the culture media can be supplemented with 1% human serum albumen (HSA). The preferred culture containers are gas permeable plastic bags, such as LifeCell (Baxter Oncology, Dearfield, Ill.).

Step 7

For the first 2 days of culture, the cells should be left undisturbed in the incubator.

Step 8

On the third day, additional microspheres and mAbs are added to the culture and mixed thoroughly. To a 100 ml culture, 100 micrograms each of anti-CD3 and anti-CD28 mAbs are added together with $3-5 \times 10^8$ coated biodegradable microspheres.

Step 9

Maintaining cells at high densities in culture with biodegradable spheres requires the frequent changing of the culture media. The high cell densities result in a high rate of build up of metabolic waste products and consumption of available nutrients. In addition, the hydrolysis of the biodegradable spheres causes the pH of the culture media to become acidic. Too rapid media replacement, however, can be detrimental to cultures where exogenous cytokines are not utilized. It is preferable not to use exogenous cytokines when processing cells for use in cell therapy protocols, as exogenous cytokines can be toxic when infused into humans and can make the cultured cells dependant upon the presence of the exogenous cytokines for viability. Therefore, the methods of the present invention include a dialysis step in the cell processing.

In order to remove 50-90% of the media and to enhance the activation state of the cultured cells, the fresh mixture of mAbs and spheres is again spun in a centrifuge as in step 5 in order to concentrate the cells enough to remove cell-free supernatant. This process can be repeated several times a day if required in order to keep the pH of the culture between 7.0 and 7.2.

Step 10

Dialysis of the removed culture medium through a membrane with a pore size of 10,000 Daltons or less will enable retention of endogenous cytokines while allowing passage of metabolic waste. In preferred embodiments, 50-90% of the culture medium of a culture is removed at least daily and 90% of the removed media passed through a dialysis filter.

Step 11

The media passed through the dialysis filter is discarded, while the 10% retained media is brought up to the original volume with fresh culture media and then added back to the T-cell/sphere culture. The retained media will contain the endogenous cytokines at the same concentrations as before the removal of the culture media.

Step 12

Steps 8 through 11 are repeated at least once a day for a minimum of 3 days (6 days total in culture). In a typical batch run of the process, the cultures are initiated with approximately $10^8$ purified CD4 cells in 100 ml of culture media volume (day 1). By the method described, the cells will expand to approximately $1-5 \times 10^9$ cells by day 6 to day 8. Upon reaching this cell number, the cells can be resuspended in 1000 ml of culture media in a gas permeable bag and steps 8 through 11 repeated at least daily for up to an additional 3 to 6 days (day 9 to day 14 of culture). Over this time, the total cells in the culture will expand to approximately $1-5 \times 10^{10}$ cells.

Harvest

The cells can be harvested any time after day 6 of culture or when at least $10^9$ cells are available in the batch culture. To assure maximal cytokine production, the timing of the harvest should occur such that the cells are formulated and infused 24 hours after the last step 8-11 cycle.

The cells produced by the methods of the invention can be aliquoted into multiple dosages of at least $10^8$ cells, preferably at least $10^9$ cells. The aliquoted dosages of cells can be frozen for storage prior to infusion. In the case of a frozen dosage form, the cells are frozen in cryoprotective media supplemented with conditioned media from the preparatory cell culture in order to maintain high cell viability. Frozen dosages are thawed, activated and formulated within 24 hours of infusion.

Formulation

The harvested cells are formulated with the activating mAbs attached to the cells surface being cross-linked with the coated biodegradable microspheres, in order to assure the cells remain activated at the time of infusion and while in circulation.

The mixture of CD4 cells and microspheres are suspended in infusion medium (e.g., isotonic solutions such as normal saline, 5% dextrose, Plasma-Lyte (Baxter) or Normasol (Abbott)). In some embodiments, the infusion medium is supplemented with 0.5%-10% human serum albumen (HSA).

The mixture is preferably adjusted to a final T-cell concentration of between $1 \times 10^7$ to $1 \times 10^8$ cells per ml of infusion media. In a preferred embodiment, $10^9$ T-cells are formulated in 100 ml of infusion media. The formulation is then packaged in one or more containers, such as syringes, plastic pouches, or plastic bottles.

Infusion

A sufficient number of formulated CD4 cells are administered to the recipient in order to ameliorate the symptoms of the disease. Typically, dosages of $10^7$ to $10^{10}$ cells are infused in a single setting, preferably dosages of $10^9$ cells. Infusions are administered either as a single $10^9$ cell dose or preferably divided into several $10^9$ cell dosages. The frequency of infusions can be every 3 to 30 days or even longer intervals if desired or indicated. The quantity of infusions is generally at least 1 infusion per patient and preferably at least 3 infusions, as tolerated, or until the disease symptoms have been ameliorated. The cells can be infused intravenously at a rate of 50-250 ml/hr.

It is important that the infused cells express high levels of FasL and CD40L. In addition to IFN-gamma, the cells should also produce the following Type 1 cytokines: IL-2, IL-15, TNF-alpha and TNF-beta. The cells should not express CTLA-4 on their surface and should not produce TGF-beta, IL-4 or IL-10. Upon co-culture with allogeneic peripheral blood mononuclear cells, the cells should cause the upregulation of Type 1 cytokines IL-1, IL-12, TNF-alpha and IFN-gamma and upregulation of MHC and co-stimulatory molecules on autologous APC and target cells. In addition, upregulation of effector molecules such as FasL, TRAIL, TWEAK and other TNFR should be evident in autologous cells after mixing with the allogeneic CD4 cells produced by the method of this invention.

Mechanism of Action

Cells resulting from the method of the invention will acutely activate cells of the innate immune system when co-cultured. This activation occurs due to interaction with CD40L expressed on the cells produced by the method of the invention and the CD40 molecule expressed on host innate immune cells. Upon co-culture of host PBMC and allogeneic donor cells produced by the method of the invention, macrophages and dendritic cells upregulate co-stimulatory cell surface molecules and MHC class I and II molecules, produce pro-inflammatory cytokines, such as IFN-gamma, TNF-alpha, IL-1, IL-12 and Type I interferons. This creates a "cytokine storm" that is nearly identical to the cytokine storm environment created by infusion of allogeneic donor lymphocytes in BMT protocols.

These characteristics combined with the ability of the activated host macrophages and dendritic cells to uptake (by phagocytosis and endocytosis) and subsequently destroy tumor cells and pathogenic organisms enables the enhanced presentation of the antigenic products of these pathogens and tumors via the MHC class I and II pathways to antigen reactive T-cells. Further, the surface phenotype of the cells produced by the method of the invention (CD45RO+, CD44+, CD62L$^{lo}$) will enable the infused cells to traffic to sites of inflammation and deliver their Type 1 cytokines to the microenvironment. This can suppress local Type 2 cytokine production, upregulate MHC Class I and II expression, co-stimulatory molecule expression and recruit tumoricidal macrophages to the tumor bed.

The high expression of FasL and TRAIL on the cells produced by the method of the invention, combined with effector activity of innate immune cells recruited to the site of inflammation or tumor bed will cause apoptosis and antigen shedding to the draining lymph nodes. The lymph nodes should be populated with activated dendritic cells from the initial CD40L/CD40 interactions and be primed to present antigens to the adaptive immune system components in a cytokine environment favorable to Type 1 immune response development. CD40L/CD40 activation of dendritic cells causes production of IL-12 and TNF-alpha by dendritic cells, cytokines which are known to bias activated naïve T-cells to Th1 and Type 1 adaptive immunity. Further, IL-12 production will further induce IFN-gamma production from T-cells and NK cells which will in turn further upregulate IL-12 from macrophages, creating an autocrine feedback loop which drives macrophage activation, T-cell maturation to Type 1 immunity and amplifies innate NK activity.

EXAMPLES

The following examples are included for illustrative purposes only and are not intended to limit the scope of the invention.

Methods:

Microsphere Preparation

The solvent evaporation method was used for preparation of microspheres. Lactel® (Birmingham Polymers, Birmingham, Ala.) 50/50 DL-PLG product number 50DG020 with a inherent viscosity of 0.15 to 0.25 dl/g was used as the polymer. The DL-PLG powder was dissolved in 20 ml of methylene chloride to a final 5% DL-PLG w/v ratio. The 5% DL-PLG solution was then added dropwise to 125 ml of 2.4% hydroxypropylmethylcellulose in 0.1M glycine/HCl buffer pH 1.1 under constant stirring at 1000 rpm at room temperature (25±2° C.). Stirring was maintained until complete evaporation of the organic solvent (about 3 hours). Microspheres were collected by centrifugation at 1000 rpm, 5 min at 40 C followed by three cycles of washing with distilled water, filtered and dried overnight. The microsphere sizes ranged from 3.0 to 7.0 um with a CV maximum of <10%. The spheres were then coated with polyclonal goat anti-mouse antibody using the absorption method. The antibody was suspended in 30 ml of PBS solution with 5% human serum albumen (HSA) at a concentration of 10 ug/ml. This solution was used to resuspend the dried microspheres at a concentration of approximately 2×108 particles per ml. The microspheres and the polyclonal antibody were mixed end over end at 40 C for 8 hours. The microspheres were then washed 3 times in PBS with HSA, filtered and dried. The dried particles were stored in a solution of 70% isopropanol prior to use.

Allogeneic Cell Product Preparation

For the examples below, Allogeneic Cell Product was prepared according to the method described in the preferred embodiments. Briefly, 1.2×10$^{10}$ peripheral blood mononuclear cells (PBMC) were collected from a healthy donor by leukapheresis. The PBMC were washed and stored a room temperature overnight. The PBMC were enriched for CD4+ cells by labeling with biotinylated anti-CD4 mAb and mixing with a secondary anti-biotin mAb magnetic particles (Miltenyi Biotec, Germany). The CD4+ cells were then selected by passing through a magnetized column (MACS®). 1.3×108 CD4+ were selected and placed in 100 ml of XVIVO-15 culture media in a Lifeflask (Baxter) gas permeable bag. The CD4+ cells were incubated overnight at 370 C in an atmosphere of 5% CO2. The following day, the non-adherent cells were washed and labeled with anti-CD3 and anti-CD28 mAbs and suspended with goat anti-mouse coated biodegradable microspheres at a 3:1 ratio. The suspension was centrifuged at 1000 rpm for 5 min and gently resuspended by manual massage of the culture bag. The suspension was incubated for 72 h, and the cells were relabeled and suspended with new microspheres. The suspension was centrifuged at 1600 rpm for 8 min, the supernatant removed and 90% of the volume passed through a dialysis filter. The retained supernatant was added back to the cell suspension and the volume brought back to 100 ml with fresh culture media. This process was repeated daily until day 9 of culture. On day 10, the resulting cells were used in the examples described below.

Example #1: Phenotypic Analysis of Allogeneic Cell Product

A sample of allogeneic cell product was taken on day 1 and day 10 for phenotypic analysis. For cell immunophenotyping, surface labeling was performed by a direct fluorescence technique using monoclonal antibodies (Becton-Dickinson, San Jose, Calif., USA), against human CD4, CD8, CD14, CD19, CD56, CD4/CD25, CD4/DR, CD4/CD45RA, CD4/CD45RO, CD4/CD62L, CD4/CD154 (FasL), CD4/TRAIL. To detect intracellular cytokines, mononuclear cells were permeabilized with FACS permeabilizing solution (Becton-Dickinson). Flow cytometry analyses were carried out with a FACSort equipment (Becton-Dickinson) using the Cellquest software. The results are reported as the percent of stained cells calculated from 10,000 events for all immunophenotypes.

Results in percentage of total cells (MFIR):

|  | DAY 1 | DAY 10 |
| --- | --- | --- |
| CD4 | 92.5 | 99.8 |
| CD8 | 0.8 | 0 |
| CD14 | 4.8 | 0 |
| CD19 | 0.9 | 0 |
| CD56 | 1.7 | 0 |
| CD4/CD25 | 2.3 | 92.9 |
| CD4/DR | 4.5 | 89.7 |
| CD4/CD45RA | 70.3 | 10.9 |
| CD4/CD45RO | 16.6 | 78.1 |
| CD4/CD62L$^{hi}$ | 69.4 | 0.9 |
| CD4/CD154 (FasL) | 0.8 | 74.3 (67) |
| CD4/TRAIL | 0.3 | 68.3 (26.6) |
| CD4/IFN-gamma | 18.6 | 98 |
| CD4/IL-4 | 4.8 | 0.2 |

These results indicate that the Allogeneic Cell Product has differentiated into a Type 1 cell with an activated memory phenotype.

Example #2: Cytokine Gene Profile of Allogeneic Cell Product

To determine the cytokine profile of the Allogeneic Cell Product, cytosolic RNA was purified using a RNeasy kit (Qiagen) and reversed transcribed using a Roche First Strand cDNA synthesis kit. Primers and probes were purchased from Applied Biosystems or were designed using Primer Express software. Real-time PCR amplification and product detection was performed according to manufacturer's recommended procedures on an ABI Prism 7700. Gene product is expressed relative to GAPDH expression, which is set at a value of 100,000 on day 1 and day 10.

|  | Day 1 | Day 10 |
| --- | --- | --- |
| IL-1beta | 85 | 7 |
| IL-2 | 4 | 18,450 |
| IL-4 | 2 | 0 |
| IL-5 | 0 | 0 |
| IL-6 | 0 | 0 |
| IL-10 | 11 | 10 |

-continued

|  | Day 1 | Day 10 |
| --- | --- | --- |
| IL-12p35 | 12 | 12 |
| IL-12p40 | 0 | 0 |
| IL-13 | 82 | 3 |
| IL-15 | 11 | 1200 |
| IL-18 | 10 | 8 |
| TNF-alpha | 21 | 84,880 |
| IFN-gamma | 18 | 94,600 |
| TGF-beta | 0 | 0 |

Example #3: Host PBMC Rejection of Allogeneic Cell Product

PBMC from a stage 3 ovarian cancer patient was prepared by density gradient purification and isolation of buffy coat. The host PBMC were mixed with Allogeneic Cell Product at a 50:50 ratio and cultured in 24 well plates for 7 days. The Allogeneic cells were labeled with green cell tracker dye, 5-chloro-methyl-fluorescein diacetate (CMFDA). The cultures were set up in triplicate.

Results:

At the end of the 7 day culture, less than 2% of the live cells in each of the wells stained green, indicating that they were rejected by the host PBMC.

Example #4: Cytokine Analysis of Mixed Host PBMC and Allogeneic Product

In order to determine the ability of the allogeneic cell product produced by the method of the invention to stimulate host cancer patient PBMC to produce Type 1 cytokines, allogeneic cells were prepared as described in the Preferred Embodiments, harvested on day 9 and mixed with $1\times10^6$ PBMC from a cancer patient in a 24 well culture plate and incubated for 48 hours at 37° C. in a humidified atmosphere containing 5% CO2.

Human PBMC were isolated by density gradient centrifugation of peripheral blood obtained from a patient with metastatic breast cancer prior to mastectomy. Allogeneic cell product was added to the PBMC cultures at ratios of 1:100, 1:50 and 1:25. PBMC in media alone was used as a negative control and PBMC activated with PHA served as the positive control.

After 48 hours, supernatant samples were removed from each well and analyzed by ELISA. Results are shown as means+/−SE of triplicate cultures in pg/ml. ND=not detectable.

Results:

|  | Media | PHA | 1:100 | 1:50 | 1:25 |
| --- | --- | --- | --- | --- | --- |
| IL-2 | 83 ± 8 | 12934 ± 24 | 18734 ± 73 | 16726 ± 82 | 12993 ± 72 |
| IL-4 | 249 ± 2 | 643 ± 12 | 32 ± 3 | ND | ND |
| IL-6 | 349 ± 12 | 1034 ± 18 | 1395 ± 15 | 1863 ± 1 | 1822 ± 18 |
| IL-10 | 874 ± 32 | 1739 ± 52 | ND | ND | ND |
| IL-12p70 | ND | 980 ± 6 | 3890 ± 54 | 4176 ± 32 | 4231 ± 31 |
| IL-15 | ND | 1628 ± 48 | 2847 ± 91 | 7493 ± 93 | 8328 ± 74 |
| IFN-alpha | 42 ± 3 | 349 ± 7 | 843 ± 34 | 938 ± 23 | 1022 ± 34 |
| IFN-gamma | ND | 380 ± 5 | 15863 ± 532 | 178745 ± 368 | 22903 ± 839 |
| TNF-alpha | ND | 1893 ± 32 | 11932 ± 323 | 12435 ± 393 | 13458 ± 239 |

The results indicate that the allogeneic cell product of the present invention can elicit strong upregulation of Type 1 cytokine production and down regulate Type 2 cytokine production.

Example #5: Phenotypic Analysis of Host Cells After Mixed with Allogeneic Product Host CD3+ T-cells and CD14+ monocytes from Example #3 were analyzed phenotypically for effector and co-stimulatory markers.

Results in percent of total PBMC (MFIR)

|  | Day 1 | Day 7 |
| --- | --- | --- |
| CD14/CD80 | 12.9 | 66.5 (5.8) |
| CD14/CD86 | 16.6 | 81.7 (922) |
| CD3/CD154 (FasL) | 0.6 | 34.3 (47) |
| CD3/TRAIL | 0.2 | 38.5 (16.6) |
| CD14/CD154 | 11.6 | 35.3 (13.8) |
| CD14/TRAIL | 4.8 | 28.4 (9.5) |

The results indicate that host cells upregulated co-stimulatory and effector molecules during the rejection of the Allogeneic Cell Product and in the presence of the Cytokine Storm.

Example #6: Stimulation of NK Cytotoxicity

NK activity against K562 target cells was assessed by a flow cytometry assay using the D10 membrane dye (Molecular Probes, Eugene, Oreg., USA) to stain live K562 cells and propidium iodide (Sigma) nuclear dye to stain dead cells. The percent of specific lysis was calculated by the formula:

$$\frac{\% \text{ dead target cells}}{100 - \% \text{ (debris and fragments)}} \times 100$$

PBMC from a cancer patient were incubated in media alone and supernatant from a 48 h co-culture of the allogeneic product and autologous PBMC at a 1:100 ratio.
Results:

Effector:Target Ratio

|  | 100 | 50 | 25 | 12.5 | 6.3 | 3.1 |
| --- | --- | --- | --- | --- | --- | --- |
| media | 8.34 | 4.32 | 2.54 | 1.08 | 0.86 | 0.34 |
| supernatant | 85.52 | 82.11 | 71.23 | 50.65 | 34.55 | 20.91 |

These results indicate that the Type 1 cytokine storm elicited by the method of the invention is capable of significantly enhancing host NK activity.

Example #7: Cytokine Storm Supernatant Effects on Tumor Immunogenicity

Cancer cell lines NCI-H23 (lung cancer), Caki-1 (renal cell cancer) and ACHN (renal cell cancer) were analyzed for expression of MHCI, MHCII, death receptors Fas and TRAIL-R2 and co-stimulatory molecules CD80 and CD86. The cell lines were then cultured in the bottom of a transwell plate. In the top well host PBMC from a normal donor and the Allogeneic Cell Product were mixed at a 100:1 cell ratio. The cultures were incubated for 96 hours.
Results:
Results in MFIR

|  | Day 0 | Day 4 |
| --- | --- | --- |
| NCI-H23 | | |
| MHCI | 220 | 780 |
| MHCII | 0.8 | 6.8 |
| CD80 | 0.4 | 4.8 |
| CD86 | 280 | 550 |
| Fas | 0.8 | 18.5 |
| TRAIL-R2 | 19.9 | 20.8 |
| ACHN | | |
| MHCI | 190 | 1387 |
| MHCII | 0.2 | 8.8 |
| CD80 | 0.4 | 3.8 |
| CD86 | 180 | 988 |
| Fas | 0.7 | 28.5 |
| TRAIL-R2 | 7.9 | 10.8 |
| Caki-1 | | |
| MHCI | 120 | 569 |
| MHCII | 0.8 | 6.8 |
| CD80 | 0.4 | 4.8 |
| CD86 | 150 | 650 |
| Fas | 0.8 | 18.5 |
| TRAIL-R2 | 1.9 | 20.8 |

These results indicate that the cytokine storm elicited by the method of the invention is capable of increasing the immunogenicity of tumor cells and their susceptibility to apoptosis.

Although the present invention has been described with reference to preferred embodiments, workers skilled in the art will recognize that changes may be made in form and detail without departing from the spirit and scope of the invention.

What is claimed is:

1. A method for stimulating a host immune response against a tumor comprising:
    selecting cells from a normal donor of which at least a portion are T-cells;
    activating and formulating said donor cells ex vivo in media suitable for infusion into a host cancer patient, wherein said cells are activated by CD3 and CD28 surface antigen cross-linking; and
    administering said activated donor cells to the host who has a 50% or less tissue match to said normal donor.

2. The method of claim 1 wherein the host immune response against the tumor includes the production of a "cytokine storm" including at least one of the following cytokines: IL-2, IL-15, TNF-alpha, TNF-beta, IL-12 and IFN-gamma.

3. The method of claim 2 wherein the selected normal donor cells are frozen prior to activation.

4. The method of claim 1 wherein the host immune response against the tumor includes activating innate cells including NK cells or macrophages.

* * * * *